US012121289B2

(12) United States Patent
Ibrahim et al.

(10) Patent No.: US 12,121,289 B2
(45) Date of Patent: Oct. 22, 2024

(54) CONDUCTION BLOCK SYSTEMS AND METHODS

(75) Inventors: Tamer Ibrahim, Pleasant Hill, CA (US); David K. Swanson, Campbell, CA (US)

(73) Assignee: AtriCure, Inc., Mason, OH (US)

( * ) Notice: Subject to any disclaimer, the term of this patent is extended or adjusted under 35 U.S.C. 154(b) by 855 days.

(21) Appl. No.: 12/463,760

(22) Filed: May 11, 2009

(65) Prior Publication Data

US 2009/0281541 A1    Nov. 12, 2009

Related U.S. Application Data

(60) Provisional application No. 61/051,975, filed on May 9, 2008.

(51) Int. Cl.
*A61B 18/14*    (2006.01)
*A61B 18/00*    (2006.01)
(Continued)

(52) U.S. Cl.
CPC .......... *A61B 18/1492* (2013.01); *A61B 5/053* (2013.01); *A61B 2017/2945* (2013.01);
(Continued)

(58) Field of Classification Search
CPC ........ A61B 18/1492; A61B 2017/2945; A61B 2018/00797; A61B 5/053;
(Continued)

(56) References Cited

U.S. PATENT DOCUMENTS 3,745,998 A    7/1973   Rose
4,224,929 A    9/1980   Furihata
(Continued)

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.
(Continued)

*Primary Examiner* — Joseph A Stoklosa
*Assistant Examiner* — Adam J Avigan
(74) *Attorney, Agent, or Firm* — Levine Bagade Han LLP

(57) ABSTRACT

Tissue treatment systems for cardiac surgical procedures can include an ablation and monitoring assembly having a first ablation element, a second ablation element, and a monitoring mechanism. Treatment methods may involve placing an ablation and monitoring assembly of the tissue treatment system at a patient tissue treatment site, applying a first ablative energy to a first tissue location via the first ablation element and a second ablative energy to a second tissue location via the second ablation element, monitoring a condition of the first tissue location with the monitoring mechanism, and modulating application of the first ablative energy to the first tissue location in response to the condition of the first tissue location while maintaining application of the second ablative energy to the second tissue location. Embodiments also include techniques for assessing a conduction delay across a lesion that involve evaluating local activation rates on various sides of a lesion.

15 Claims, 13 Drawing Sheets

(51) Int. Cl.
  *A61B 18/18* (2006.01)
  *A61B 5/053* (2021.01)
  *A61B 17/29* (2006.01)
  *A61B 18/02* (2006.01)
  *A61B 18/10* (2006.01)
  *A61B 18/20* (2006.01)
  *A61B 90/00* (2016.01)
  *A61N 7/02* (2006.01)

(52) U.S. Cl.
  CPC .......... *A61B 2018/00005* (2013.01); *A61B 2018/00291* (2013.01); *A61B 2018/00357* (2013.01); *A61B 2018/00375* (2013.01); *A61B 2018/00577* (2013.01); *A61B 2018/00642* (2013.01); *A61B 2018/00702* (2013.01); *A61B 2018/00791* (2013.01); *A61B 2018/00797* (2013.01); *A61B 2018/00821* (2013.01); *A61B 2018/00839* (2013.01); *A61B 18/02* (2013.01); *A61B 18/10* (2013.01); *A61B 2018/1432* (2013.01); *A61B 18/1445* (2013.01); *A61B 2018/145* (2013.01); *A61B 2018/1475* (2013.01); *A61B 18/18* (2013.01); *A61B 18/20* (2013.01); *A61B 2090/065* (2016.02); *A61N 7/022* (2013.01)

(58) Field of Classification Search
  CPC .... A61B 2018/145; A61B 2018/00291; A61B 2018/00791; A61B 18/20; A61B 2018/00702; A61B 2018/00357; A61B 18/18; A61B 2018/00577; A61B 2018/00821; A61B 18/10; A61B 2018/00351; A61B 2018/00839; A61B 5/0422; A61B 2018/1467; A61B 2018/00375; A61B 2018/00642; A61B 2018/00363; A61B 5/046; A61B 5/4836; A61B 2018/00666; A61B 2018/00714; A61B 5/0402; A61B 2017/00022; A61B 2017/00243; A61B 2018/00875; A61B 18/1206; A61B 5/0464; A61B 18/14; A61B 18/1442; A61B 2018/126; A61B 2018/00886; A61B 2018/00827; A61N 7/022; A61N 1/056; A61N 1/06; A61N 1/05; A61N 1/0587; A61F 7/12
  USPC ..... 606/41–50; 607/101–102, 116, 119–132; 600/374; 128/898
  See application file for complete search history.

(56) References Cited

U.S. PATENT DOCUMENTS

| | | | |
|---|---|---|---|
| 4,445,892 A | 5/1984 | Hussein et al. | |
| 4,961,738 A | 10/1990 | Mackin | |
| 4,991,578 A | 2/1991 | Cohen | |
| 5,336,252 A | 8/1994 | Cohen | |
| 5,409,483 A | 4/1995 | Campbell et al. | |
| 5,423,805 A | 6/1995 | Brucker et al. | |
| 5,503,617 A | 4/1996 | Jako | |
| 5,593,405 A | 1/1997 | Osypka | |
| 5,672,153 A | 9/1997 | Lax et al. | |
| 5,727,569 A | 3/1998 | Benetti et al. | |
| 5,782,746 A | 7/1998 | Wright | |
| 5,785,706 A * | 7/1998 | Bednarek | 606/41 |
| 5,807,243 A | 9/1998 | Vierra et al. | |
| 5,836,311 A | 11/1998 | Borst et al. | |
| 5,865,730 A | 2/1999 | Fox et al. | |
| 5,927,284 A | 7/1999 | Borst et al. | |
| 5,976,132 A | 11/1999 | Morris | |
| 6,013,027 A | 1/2000 | Khan et al. | |
| 6,015,378 A | 1/2000 | Borst et al. | |
| 6,027,500 A * | 2/2000 | Buckles et al. | 606/34 |
| 6,036,641 A | 3/2000 | Taylor et al. | |
| 6,036,685 A | 3/2000 | Mueller | |
| 6,039,733 A | 3/2000 | Buysse et al. | |
| 6,086,586 A | 7/2000 | Hooven | |
| 6,110,106 A | 8/2000 | MacKinnon et al. | |
| 6,161,543 A | 12/2000 | Cox et al. | |
| 6,237,605 B1 | 5/2001 | Vaska et al. | |
| 6,251,065 B1 | 6/2001 | Kochamba et al. | |
| 6,277,065 B1 | 8/2001 | Donofrio | |
| 6,309,349 B1 | 10/2001 | Bertolero et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,338,738 B1 | 1/2002 | Bellotti et al. | |
| 6,346,077 B1 | 2/2002 | Taylor et al. | |
| 6,346,104 B2 * | 2/2002 | Daly et al. | 606/34 |
| 6,350,229 B1 | 2/2002 | Borst et al. | |
| 6,352,534 B1 | 3/2002 | Paddock et al. | |
| 6,364,826 B1 | 4/2002 | Borst et al. | |
| 6,371,906 B1 | 4/2002 | Borst et al. | |
| 6,390,976 B1 | 5/2002 | Spence et al. | |
| 6,394,948 B1 | 5/2002 | Borst et al. | |
| 6,463,332 B1 | 10/2002 | Aldrich | |
| 6,464,630 B1 | 10/2002 | Borst et al. | |
| 6,482,151 B1 | 11/2002 | Vierra et al. | |
| 6,484,727 B1 | 11/2002 | Vaska et al. | |
| 6,511,416 B1 | 1/2003 | Green, II et al. | |
| 6,514,250 B1 | 2/2003 | Jahns et al. | |
| 6,522,905 B2 | 2/2003 | Desai | |
| 6,524,338 B1 | 2/2003 | Gundry | |
| 6,527,767 B2 | 3/2003 | Wang et al. | |
| 6,544,263 B2 | 4/2003 | Morgan et al. | |
| 6,595,989 B1 | 7/2003 | Schaer | |
| 6,599,237 B1 | 7/2003 | Singh | |
| 6,645,202 B1 | 11/2003 | Pless et al. | |
| 6,652,518 B2 | 11/2003 | Wellman et al. | |
| 6,758,809 B2 | 7/2004 | Briscoe et al. | |
| 6,761,716 B2 * | 7/2004 | Kadhiresan et al. | 606/34 |
| 6,849,075 B2 | 2/2005 | Bertolero et al. | |
| 6,890,295 B2 | 5/2005 | Michels et al. | |
| 7,018,328 B2 | 3/2006 | Mager et al. | |
| 7,226,448 B2 | 6/2007 | Bertolero et al. | |
| 7,237,555 B2 | 7/2007 | Kochamba et al. | |
| 7,338,434 B1 | 3/2008 | Haarstad et al. | |
| 7,542,807 B2 | 6/2009 | Bertolero et al. | |
| 7,594,915 B2 | 9/2009 | Kochamba et al. | |
| 2002/0026094 A1 | 2/2002 | Roth | |
| 2002/0056460 A1 | 5/2002 | Boyd | |
| 2002/0058870 A1 * | 5/2002 | Panescu et al. | 600/424 |
| 2002/0068855 A1 | 6/2002 | Daniel et al. | |
| 2002/0099270 A1 | 7/2002 | Taylor et al. | |
| 2002/0099390 A1 | 7/2002 | Kaplan | |
| 2002/0177846 A1 | 11/2002 | Mulier et al. | |
| 2003/0009080 A1 | 1/2003 | Peng et al. | |
| 2003/0010346 A1 | 1/2003 | Paolitto et al. | |
| 2003/0060685 A1 | 3/2003 | Houser et al. | |
| 2003/0158463 A1 | 8/2003 | Julian et al. | |
| 2003/0158464 A1 | 8/2003 | Bertolero | |
| 2004/0059325 A1 * | 3/2004 | Swanson | 606/41 |
| 2005/0010179 A1 | 1/2005 | Bertolero et al. | |
| 2005/0119545 A1 * | 6/2005 | Swanson | 600/374 |
| 2005/0119653 A1 | 6/2005 | Swanson | |
| 2005/0119654 A1 | 6/2005 | Swanson et al. | |
| 2005/0240175 A1 | 10/2005 | Bertolero et al. | |
| 2006/0015165 A1 | 1/2006 | Bertolero et al. | |
| 2006/0155272 A1 | 7/2006 | Swanson | |
| 2006/0155273 A1 * | 7/2006 | Swanson | A61B 18/1442 606/51 |
| 2007/0185479 A1 * | 8/2007 | Lau | 606/33 |
| 2007/0233226 A1 | 10/2007 | Kochamba et al. | |
| 2008/0294154 A1 | 11/2008 | Ibrahim et al. | |
| 2009/0048591 A1 | 2/2009 | Ibrahim et al. | |
| 2009/0076501 A1 | 3/2009 | Bertolero et al. | |

(56) References Cited

U.S. PATENT DOCUMENTS

2009/0076537 A1   3/2009   Bertolero
2009/0163768 A1   6/2009   Ibrahim et al.

OTHER PUBLICATIONS

Jansen, Erik, et al., "Less Invasive off-pump CABG using a suction device for immobilization: The Octopus method," European Journal of Cardiothoracic surgery 12 (1997) pp. 406-412.

* cited by examiner

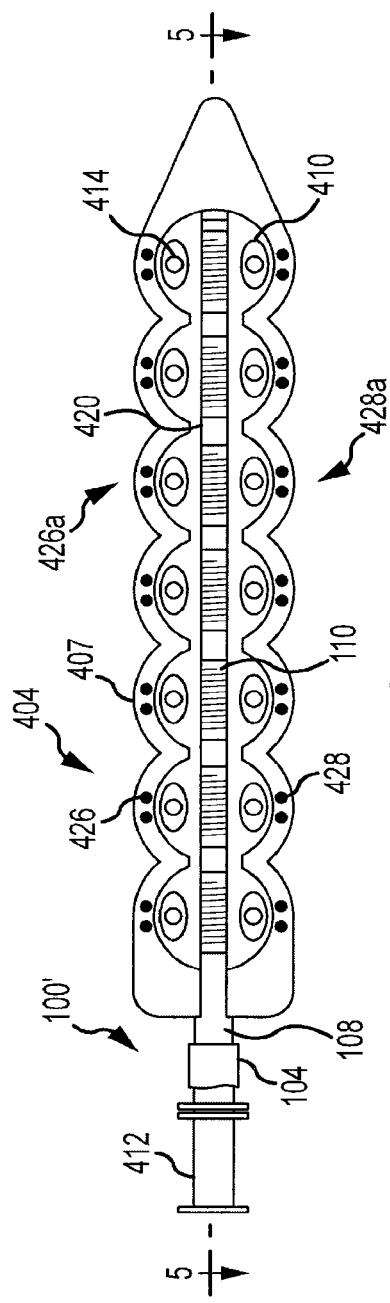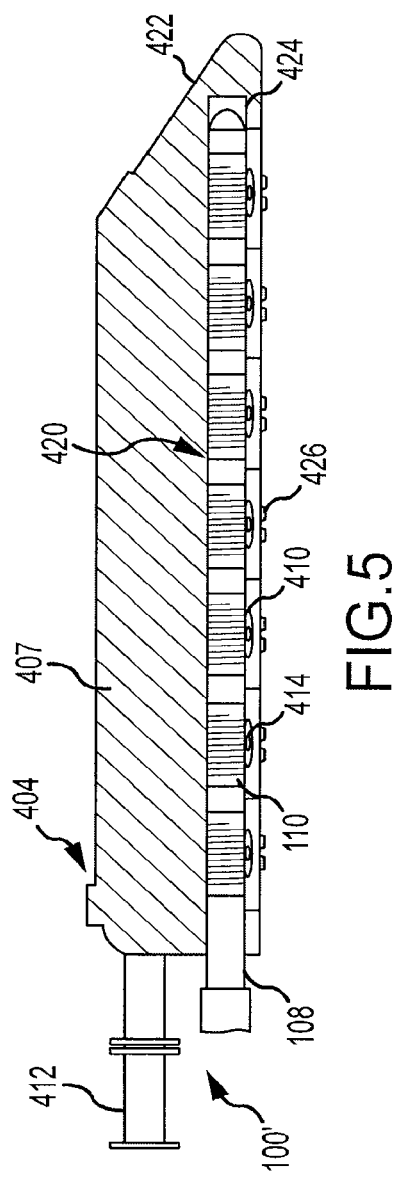

CONDUCTION BLOCK SYSTEMS AND METHODS

CROSS-REFERENCES TO RELATED APPLICATIONS

This application is a nonprovisional of, and claims the benefit of the filing date of, U.S. Provisional Patent Application No. 61/051,975 filed May 9, 2008. This application is also related to U.S. patent application Ser. No. 11/186,149 filed Jul. 20, 2005, the contents of which are incorporated herein by reference.

BACKGROUND OF THE INVENTION

Embodiments of the present invention relate generally to medical devices and methods. More specifically, embodiments relate to devices and methods to evaluate electrical conduction block across ablation lesions in cardiac tissue.

Atrial fibrillation (AF) can refer to a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy, and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3%/year of those aged 50-59 to more than 7%/year of those aged 80 and over. AF is responsible for up to 35% of the strokes that occur in people older than age 85. Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under-prescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists often classify AF by the "three Ps": paroxysmal, persistent, or permanent. Paroxysmal AF, typically characterized by sporadic, usually self-limiting episodes lasting less than 48 hours, is usually the most amenable to treatment, while persistent or permanent AF can be much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is often characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating epicardial tissue to treat AF and other arrhythmias. For example, with currently available devices and methods it may be difficult to modulate or control the amount of ablation energy applied to cardiac tissue during an AF treatment. In some cases, insufficient amounts of ablation energy are applied. In other cases, excessive amounts of ablation energy are applied.

Therefore, a need exists for improved devices and methods for ablating epicardial tissue to treat AF and other cardiac arrhythmias. Preferably, such devices and methods would provide careful control or modulation of ablation energy to the tissue, so that appropriate amounts of energy are applied at desired locations. For example, during a procedure it may be desirable to apply a lesser amount of ablation energy, or possibly no ablation energy at all, at one location, while applying a greater amount of ablation energy at another location. Such devices and methods might also provide additional advantages, such as advantageous ablation patterns, conduction block or contact evaluation, and the like. At least some of these objectives will be met by the present invention.

BRIEF SUMMARY OF THE INVENTION

Devices and methods of the present invention provide for ablation of cardiac tissue for treating cardiac arrhythmias such as atrial fibrillation. Although the devices and methods are often used to ablate epicardial tissue in the vicinity of at least one pulmonary vein, various embodiments may be used to ablate other cardiac tissues in other locations on a heart. Generally, devices of the invention often include a tissue contacting member for contacting a portion of the epicardial tissue of a heart and securing the ablation device to the epicardial tissue, and an ablation member for ablating at least a portion of the tissue. In various embodiments, the devices have features which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive incisions, introducer devices and the like. Although much of the following description focuses on using certain device and method embodiments of the present invention to treat atrial fibrillation (AF) by ablating epicardial tissue on a human heart, the devices and methods may be used in veterinary or research contexts, to treat various heart conditions other than atrial fibrillation and/or to ablate cardiac tissue other than the epicardium.

In one aspect, embodiments of the present invention encompass methods of operating a tissue treatment system during a cardiac surgical procedure. Methods may include, for example, placing an ablation and monitoring assembly of the tissue treatment system at a patient tissue treatment site. The ablation and monitoring assembly can include a first ablation element, a second ablation element, and a monitoring mechanism. Methods may also include applying a first ablative energy to a first tissue location via the first ablation element and a second ablative energy to a second tissue location via the second ablation element, and monitoring a condition of the first tissue location with the monitoring mechanism. Methods may also include modulating application of the first ablative energy to the first tissue location in response to the condition of the first tissue location while maintaining application of the second ablative energy to the second tissue location. In some cases, a monitoring process or step may include delivering a stimulation energy to the first tissue location, and detecting with the monitoring mechanism whether a tissue near the first tissue location is sufficiently stimulated in response to the stimulation energy. In some cases, a determining process or step may include evaluating an electrocardiogram of the tissue near the first tissue location. Optionally, a monitoring process or step may include visually inspecting the tissue near the first tissue location. A monitoring mechanism may include one or more stimulation electrodes. A patient tissue treatment site can include epicardial tissue at or near one or more pulmonary veins of the patient. In some instances, methods may include placing the ablation and monitoring assembly at the patient tissue treatment site with an obturator and introducer assembly. A tissue treatment system can include, for example, a tissue contacting assembly. Relatedly, an ablation and monitoring assembly may be at least partially disposed within the tissue contacting assembly. Methods may also include determining whether the ablation and monitoring assembly is in sufficient contact with the patient tissue treatment site. In some embodiments, methods include a monitoring process or step that involves detecting a conduction block at the first tissue location. Methods may further involve contacting the patient tissue treatment site with a suction mechanism of the tissue treatment system. According to some method embodiments, the first ablation element may include a monopolar electrode. Relatedly, the first ablation element may include a bipolar electrode.

In another aspect, embodiments of the present invention include a tissue treatment system for applying a treatment to a patient during a cardiac surgical procedure. An exemplary tissue treatment system may include an ablation and monitoring assembly having a first ablation element configured to deliver ablation energy to a first tissue location, a second ablation element configured to deliver ablation energy to a second tissue location, and a monitoring mechanism. The system may also include a processor coupled with the ablation and monitoring assembly, and a memory coupled with the processor. The memory can be configured to store a plurality of code modules for execution by the processor. The plurality of code modules can include, for example, an input module that receives conduction block information from the monitoring mechanism, and a calculation module that determines a first amount of ablative energy delivered through the first ablation element and a second amount of ablative energy delivered through the second ablation element based on the conduction block information. According to some embodiments, the calculation module can be configured to reduce the first amount of ablative energy when the conduction block information indicates a conduction block at the first tissue location.

In another aspect, embodiments encompass methods of operating a tissue treatment system during a cardiac surgical procedure, whereby the methods include, for example, placing an ablation and monitoring assembly of the tissue treatment system at a patient tissue treatment site. The ablation and monitoring assembly can include an ablation element monitoring mechanism. Methods may also include applying a first ablative energy to a first tissue location via a first portion of the ablation element and a second ablative energy to a second tissue location via a second portion of the ablation element, monitoring a condition of the first tissue location with the monitoring mechanism, and modulating application of the first ablative energy to the first tissue location in response to the condition of the first tissue location while maintaining application of the second ablative energy to the second tissue location.

In a further aspect, embodiments of the present invention encompass methods of assessing a conduction delay across a lesion. Assessment methods may include, for example, evaluating a first local activation rate at a first site on a first side of the lesion, evaluating a second local activation rate at a second site on a second side of the lesion, performing a pacing procedure to assess the conduction delay if both the first local activation rate and the second local activation rate are less than a predetermined excitation rate, and performing a sensing procedure to assess the conduction delay if either of the first local activation rate or the second local activation rate exceed the predetermined excitation rate. In some cases, a sensing procedure can involve evaluating the variability of multiple intervals between local excitations on the first side of the lesion, and evaluating the variability of multiple intervals between local excitations on the second side of the lesion. In some cases, a sensing procedure can involve evaluating the average of multiple activation intervals on the first side of the lesion, and evaluating the average of multiple activation intervals on the second side of the lesion. Optionally, a sensing procedure can involve evaluating the time of arrival of multiple activations on the first side of the lesion, and evaluating the time of arrival of multiple activations on the second side of the lesion.

BRIEF DESCRIPTION OF THE DRAWINGS

FIG. 4 illustrates aspects of an ablation and monitoring assembly according to embodiments of the present invention.

FIG. 5 illustrates aspects of an ablation and monitoring assembly according to embodiments of the present invention.

DETAILED DESCRIPTION OF THE INVENTION

Figure 1:
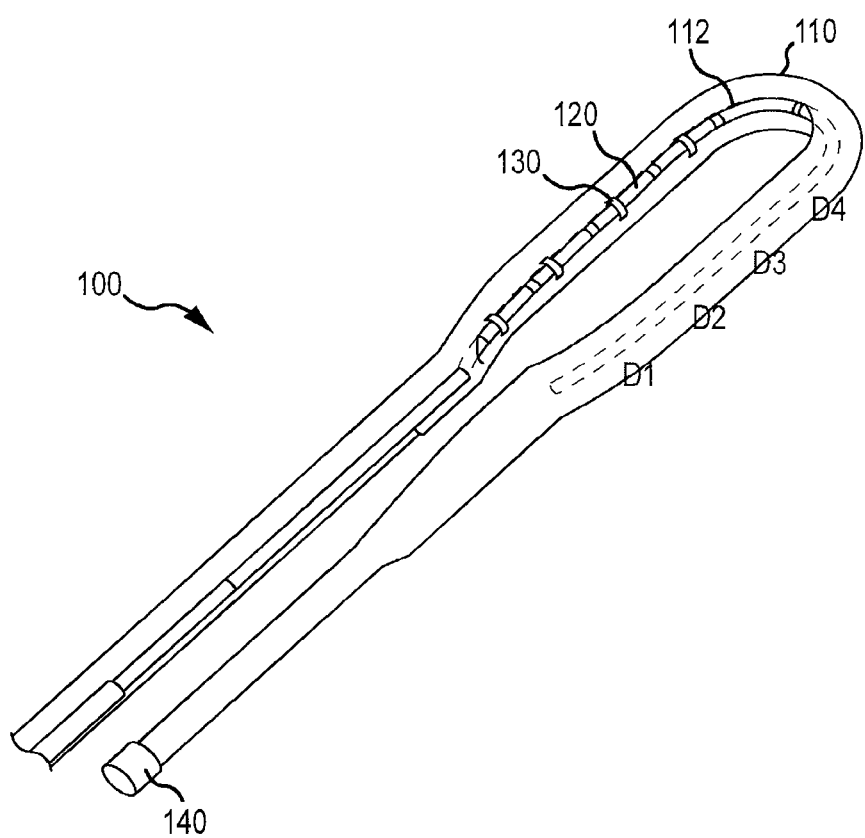
FIG. 1 illustrates aspects of a tissue treatment system according to embodiments of the present invention.

Embodiments of the present invention relate generally to medical devices and methods and more specifically to devices and methods for ablating cardiac tissue for treating cardiac arrhythmias such as atrial fibrillation. Ablation of cardiac tissue in various patterns has been shown to disrupt conduction pathways in the heart to ameliorate or eliminate AF or other arrhythmias. Devices and methods disclosed herein will often be used to ablate epicardial tissue in the vicinity of at least one pulmonary vein, but various embodiments may be used to ablate other cardiac tissues in other locations on a heart.

Generally, ablation device embodiments may include at least one tissue contacting member for contacting a portion of the epicardial tissue of a heart, securing means for securing the ablation device to the tissue, and at least one ablation member coupled with the contacting member for ablating at least a portion of the tissue. In various embodiments, the devices have features which enable the device to attach to the epicardial surface with sufficient strength to allow the tissue to be stabilized via the device. For example, some embodiments may use suction force to secure the device to epicardial tissue and stabilize a beating heart to enable a beating heart ablation procedure. Embodiments may include other features, such as sensors for sensing whether tissue has been ablated, a support member with an arm for connecting the device to a positioning device, a cooling apparatus for cooling epicardial tissue, visualization devices and the like. Some embodiments of the device are introducible into a patient via minimally invasive means, such as a minimally invasive incision, sheath, trocar or the like. Ablation device embodiments may be configured for use in minimally invasive procures, and may be longer than two feet. A majority of the probe may rest outside of the patient while the active ablation portion of the device is inserted via minimally invasive incision.

Embodiments also includes ablation systems having an ablation energy source for providing energy to the ablation device. An ablation energy source is typically suited for use with ablation apparatus as described herein using RF energy. With regard to RF ablation, a typical RF ablation system includes a RF generator which feeds current to an ablation device, including those described in this application, containing a conductive electrode for contacting targeted tissue. The electrical circuit can be completed by a return path to the RF generator, provided through the patient and a large conductive plate, which is typically in contact with the patient's back. Embodiments encompass ablation using RF electrodes, including single RF ablation electrodes. Although ablation energy is often described herein in terms of RF energy, it is understood that embodiments are not limited to such ablation modalities, and other kinds of ablation energy sources and ablation devices may be used. Hence, embodiments of the present invention encompass any of a variety of ablation techniques, including without limitation infrared lasers, high intensity focused ultrasound (HIFU), microwave, cryoablation (killing or damaging the tissue by freezing), chemical or biological agents, radiation, and the like. With regard to such ablation techniques, other suitable ablation elements or mechanisms, instead or in addition to an RF electrode, can be used. Hence, these approaches can involve the selective activation or modulation of individual ablation elements of the ablation system.

Method embodiments generally include contacting a device with epicardial tissue, using a tissue contacting member on the device to secure the device to the tissue, and ablating the tissue with an ablation member on the device. In some embodiments, the method further includes additional steps such as positioning the device on the epicardial tissue, stabilizing cardiac tissue, cooling cardiac tissue, positioning the device using a positioning device, visualizing epicardial tissue with an imaging device and the like. Again, although much of the following description focuses on embodiments used to treat AF by ablating epicardial tissue near one or more pulmonary veins on a human heart, the devices and methods may be used in veterinary or research contexts, to treat various heart conditions other than AF, to ablate cardiac tissue other than the epicardium and/or in any other suitable manner or context.

Referring now to the drawings, FIG. 1 illustrates aspects of a tissue treatment system according to embodiments of the present invention. Tissue treatment system 100 is well suited for use in medical procedures that involve ablating cardiac tissue of a human heart, such as those techniques disclosed in U.S. Patent Application Nos. 60/939,201 filed: May 21, 2007, and 61/015,472 filed Dec. 20, 2007. The content of each of these applications is incorporated herein by reference. Tissue treatment system 100 includes a tissue contacting assembly 110, optionally having a suction pod 112. Tissue treatment system 100 also includes an ablation and monitoring assembly 120 that extends through a length of the tissue contacting assembly. In some cases, tissue treatment system 100 also includes one or more holders 130 that can hold ablation and monitoring assembly 120 within or relative to tissue contacting assembly 110. Typically, during a surgical procedure the ablation and monitoring assembly is coupled with an energy source. When a treatment or medical procedure is completed, the ablation and monitoring assembly may be decoupled from the energy source.

According to some embodiments, a treatment method may include ablating and monitoring a cardiac tissue of a patient with tissue treatment system 100. Treatment methods may also include techniques for placing tissue treatment system 100 at a desired location within a patient. For example, a treatment method may include positioning tissue treatment system 100 at or near the pulmonary veins of a patient. A surgeon or operator may use an obturator and introducer assembly to posit the tissue treatment system at or near a specific location or anatomical feature of the patient. Ablation and monitoring assembly 120 can include any of a variety of tissue ablation mechanisms. In some cases, an ablation and monitoring assembly 120 can include an ablation element that transmits or delivers RF energy to patient tissue. Optionally, suitable ablation elements can transmit or deliver infrared laser energy, high intensity focused ultrasound (HIFU) energy, microwave energy, cryoablation energy, and the like. Embodiments encompass ablation and monitoring assemblies having multiple ablation elements, such as RF electrodes. In some cases, an ablation and monitoring assembly may include a single ablation element, such as a single RF ablation electrode. Typically, an RF electrode is activated in its entirety during an ablation procedure. Longer lesion lengths can be made by moving the electrode and ablating so that the ablations from the two ablation applications overlap. The procedure can be repeated until the desired lesion pattern is completed.

Figure 2:
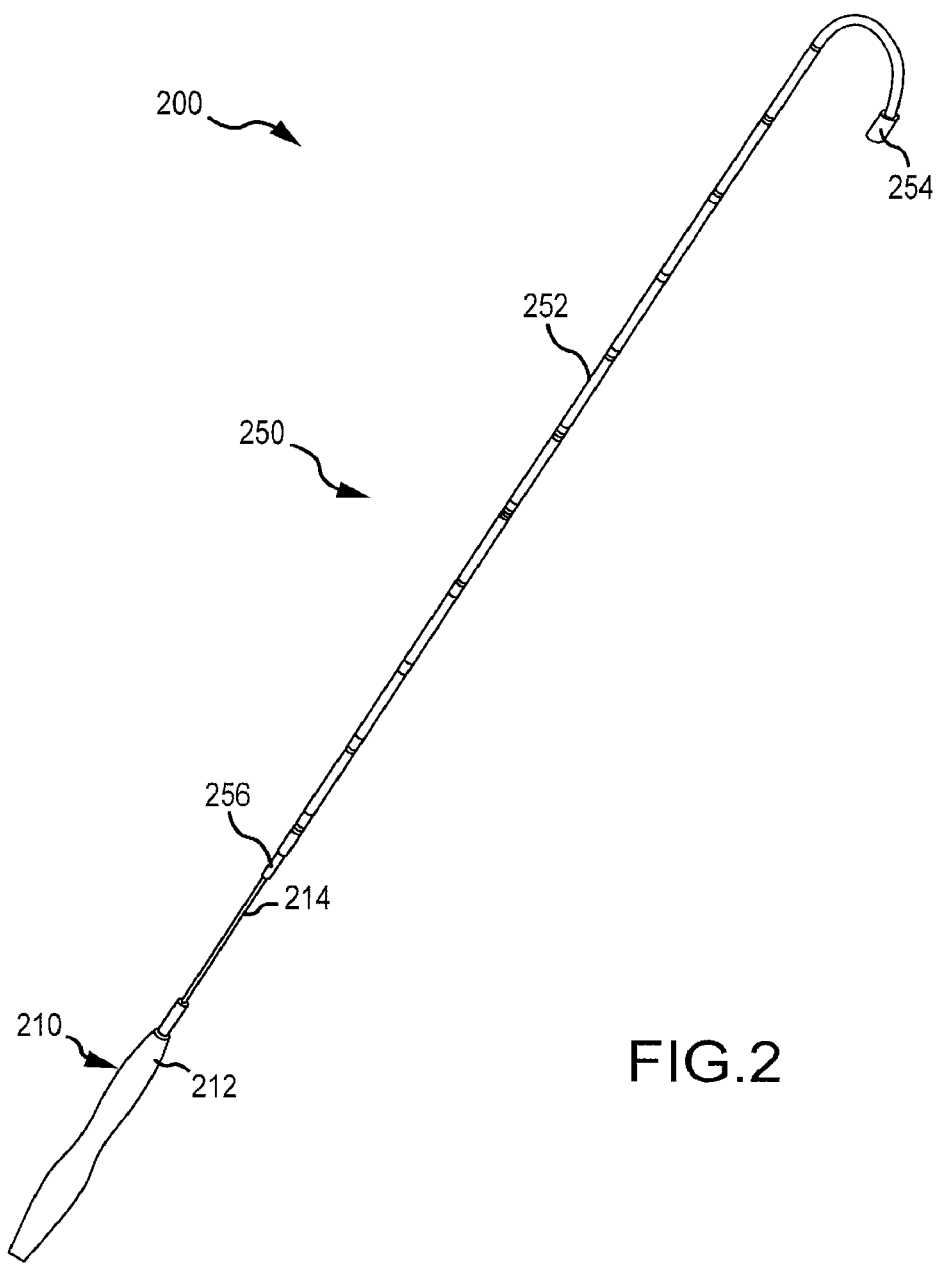
FIG. 2 depicts an obturator and introducer assembly according to embodiments of the present invention.

FIG. 2 depicts an obturator and introducer assembly 200 according to embodiments of the present invention. Obturator and introducer assembly 200 includes an obturator 210 and an introducer 250. The introducer includes a tube 252 that is pre-bent or pre-formed into a particular shape, for example a curved or J shape. The obturator includes a handle 212 and a shaft 214. As shown here, obturator shaft 214 can be inserted into introducer tube 252, so that shaft 214 extends substantially through a length of tube 252. The introducer can be fabricated with a relatively flexible material, and the obturator can be fabricated with a relatively rigid material, so that when the obturator is inserted into the introducer, the introducer conforms to or toward the shape of the obturator. When obturator shaft 214 is removed from introducer tube 252, the tube can return to its preformed or pre-bent shape. A distal end 254 of introducer 250 can have a designated region for grasping. During a medical procedure, a grasping instrument may be introduced through the same or a second incision to grasp the distal end or portion 254 of the introducer 250. An operator or surgeon can use the grasping instrument to pull distal end or portion 254 of the introducer outside the body of the patient. A distal end or portion 140 of the tissue treatment system shown in FIG. 1 can be attached with a proximal end or portion 256 of the introducer. Thus, the introducer can be withdrawn or otherwise maneuvered until the tissue treatment system is positioned at or near a desired location within the patient.

According to some embodiments, a treatment method may include inserting an obturator into an introducer, and advancing the combined obturator and introducer assembly through a first incision into the transverse sinus cavity. When the combined assembly has been positioned in a desired area or location at or near the pulmonary veins, the obturator can be withdrawn from the introducer, and the introducer can be allowed to assume a pre-formed shape which may at least partially reach around the pulmonary veins, possibly also guided by contact with the pericardium. In some cases, the introducer is long enough to be inserted from thoracotomy into transverse sinus cavity around the pulmonary veins and out through the oblique sinus and out through the same or a different thoracotomy. Another instrument can be advanced through the same or different thoracotomy to grasp the distal end of the introducer. The introducer can be pulled around the pulmonary veins until the distal end is outside the body of the patient. At this point, both the proximal and distal ends of the introducer can be disposed outside the body of the patient.

A proximal end of introducer can be attached, for example with a luer fitting, to the distal end of a tissue treatment system. The introducer, the tissue treatment system, or both, may include indication markers and lines which an operator can use or rely upon when positioning the tissue treatment system, so as to ensure the desired or proper placement. For example, circumferential indication markers on the introducer can be used as depth measurements, and an indication stripe on the surface of the introducer can be aligned with similar markings on the tissue treatment system to insure that the ablation device will be facing properly when inserted. In some embodiments, the introducer can have torsional rigidity to facilitate steerability. Further, the introducer can include a material having a highly visible color for endoscopic visualization and distinguishing from natural anatomical colors.

Once the tissue treatment system is in position, suction can be applied to adhere the ablation device to the tissue surrounding the pulmonary veins. The tissue treatment system can be placed into position via any of a variety of suitable techniques, such as those described in U.S. Patent Application Nos. 60/939,201 and 61/015,472 filed May 21, 2007 and Dec. 20, 2007, respectively. The content of each filing is incorporated herein by reference. Ablation energy can be applied. Once treatment is complete, the tissue treatment system can be removed.

According to some embodiments, treatment methods may include performing a medical procedure that entails creating a continuous lesion encircling or partially encircling the pulmonary veins to electrically isolate the pulmonary veins. Treatment methods may also include creating ablation lesions in the left and/or right atrium, vena cava, endocardium to the mitral valve annulus, or along the left atrial appendage to create a Maze-like lesion set for treatment of atrial fibrillation.

Figure 3:
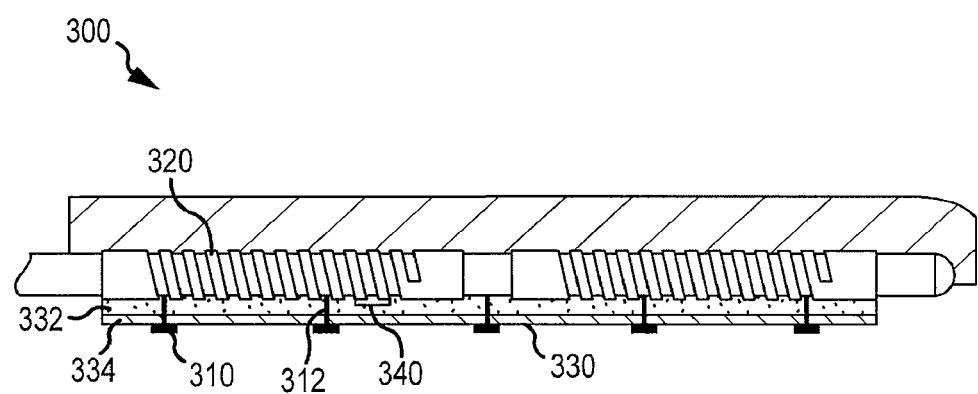
FIG. 3 illustrates aspects of an ablation and monitoring assembly according to embodiments of the present invention.

FIG. 3 illustrates aspects of an ablation and monitoring assembly 300 according to embodiments of the present invention. Such systems can include one or more stimulation electrode for pacing or stimulating tissue. Stimulation electrodes may be used to perform a variety of functions before, during, and after a lesion formation procedure. For example, stimulation electrodes may be used to confirm tissue contact prior to supplying coagulation energy, to evaluate the lesion as the coagulation energy is supplied, and to confirm whether or not a therapeutic lesion has been formed after the coagulation energy has been discontinued. Stimulation energy may be used because non-viable tissue, for example coagulated tissue, is difficult or impossible to stimulate and typically will not propagate stimulation energy to nearby tissue.

Hence, ablation and monitoring assembly 300 as depicted in FIG. 3 includes one or more stimulation electrodes 310 that are capable of providing pulses of energy that stimulate, but do not coagulate, tissue. Power delivered to tissue for stimulation purposes will typically be significantly less than that which would form a transmural or otherwise therapeutic lesion in tissue. An exemplary stimulation energy delivery can include two stimulation pulses per second, each pulse being 1 millisecond. In some embodiments, the amplitude can be 10 mA, which would create 5 V, for a total power delivery of 100 µW. In contrast, the amount of power used for coagulating tissue can often range from about 5 to about 150 W. The amplitude may be increased in some instances, for example where the stimulation pulses are being supplied at the same time as the tissue coagulation energy. Ablation and monitoring assembly 300 also includes one or more ablation or coagulation electrodes 320. The stimulation electrodes can be disposed on energy transmission surfaces of a variable spacing structure 330. Alternatively, the stimulation electrodes may be located between a resilient member 332 and a barrier member 334 or, in instances where there is no barrier member, simply on the exterior of resilient member 332. The stimulation electrodes may also be used in conjunction with a resilient member that includes conductive fibers. A stimulation electrode 310 may be connected with a signal wire 312. Optionally, a signal wire can be configured such that it will not change the mechanical properties of the resilient material. Suitable signal wires can include wires that are 38 gauge or smaller. Ablation and monitoring assembly may also include one or more sensors 340, such as temperature sensors.

As shown here, signal wire 312 traverses resilient material 332 and can enter a support structure near stimulation electrode 310. For example, a portion of signal wire 312 can be disposed between the windings of an underlying coagulation electrode 320, between two adjacent underlying coagulation electrodes 320, or just proximal to an underlying coagulation electrode 320. A signal line or wire 312 can be configured to provide connectivity between stimulation electrode 310 and an EP recording apparatus. One or more stimulation electrodes can be positioned such that they are located between, and aligned with, one or more coagulation electrodes. In some cases, a stimulation electrode can be aligned with a channel, such as a linear channel, and the stimulation electrode can face the same direction, and the same tissue, as a temperature sensor 340.

The placement of tissue stimulation electrodes on the same surgical device as the tissue coagulation electrodes allows the physician to quickly and easily confirm tissue contact and evaluate the lesion with little or no movement of the device. Stimulation electrodes can be located between the energy transmitting portions of ablation and monitoring assembly 300 and can also be located in a current path between ablation and monitoring assembly 300 and the tissue. This arrangement can provide accurate information when the stimulation electrodes are used to confirm tissue contact prior to supplying coagulation energy, because the stimulation electrodes are in contact with the portions of the tissue structure through which current will be transmitted, as opposed to being in contact with tissue that may be further from the current path.

The location of the stimulation electrodes can also provide accurate information concerning the lesion itself during and after the tissue coagulation procedure because the stimulation electrodes are in direct contact with the coagulated tissue. The assessment of the lesion can be localized. For example, the assessment can be made directly on the target tissue within the current path. Therefore, a lesion assessment process can be easier to implement than those which involve stimulating tissue on one side of a lesion and sensing tissue on the other. Here, the assessment can involve a determination whether or not stimulation of the tissue adjacent to the lesion occurs, as opposed to an assessment of the propagation delay between the stimulation pulse on one side of the lesion and the stimulation on the other.

With respect to methods by which tissue contact may be confirmed after the physician has positioned ablation and monitoring assembly 300 on a tissue structure, the stimulation electrodes may be used to supply pulses of stimulation energy, sometimes referred to as pacing pulses, to the tissue in the current path CP between ablation and monitoring assembly 300 and the tissue. The stimulation energy can be supplied through one or more single stimulation electrodes. The physician can monitor the adjacent tissue, either visually or with a monitor such as an ECG to determine whether that tissue was stimulated. In the context of the treatment of atrial fibrillation, for example, the procedure may be performed after ablation and monitoring assembly 300 is epicardially positioned about one or more of the pulmonary veins. If the stimulation energy stimulates, or paces, the adjacent tissue, for example the left atrium, the physician can know that proper contact has been achieved for the associated portions of ablation and monitoring assembly 300. This process may be sequentially repeated with any desired combination of stimulation electrodes to insure or evaluate tissue contact with the other portions of ablation and monitoring assembly 300. Thereafter, and without moving ablation and monitoring assembly 300, tissue coagulation energy may be applied to the tissue in the current path with one or more coagulation electrodes to form a lesion.

Stimulation energy can be used while the tissue coagulation energy is being supplied in order to determine when a transmural lesion has been completely formed. Here, stimulation energy pulses may be supplied by stimulation electrodes to the tissue in the current path. The tissue adjacent to the current path can be monitored, either visually or with an ECG, to determine when the adjacent tissue is no longer being stimulated. The supply of tissue coagulation energy may be discontinued in response to such a determination. For example, if a tissue treatment system is programmed to supply coagulation energy for 30 seconds, the supply of energy could end after 25 seconds if the lesion is completed earlier than was anticipated, as determined by the inability to stimulate the adjacent tissue. This may be accomplished either manually or automatically.

Tissue may become non-stimulatable before it is irreversibly coagulated or otherwise irreversibly damaged. Accordingly, tissue coagulation energy can continue to be supplied for a few seconds after the adjacent tissue ceases to be stimulated by stimulation energy pulses. That is, there can be a brief delay before the coagulation energy is discontinued. It should also be noted that while coagulation energy is being supplied by the coagulation electrodes, the stimulation energy can be supplied at a significantly higher amplitude, for example 5 times higher, than it would be before or after the coagulation procedure because tissue that is heated can be harder to stimulate. For example, if 4 mA pulses are suitable before and after the coagulation procedure, then 20 mA pulses can be used during the coagulation procedure.

Stimulation energy may be supplied after tissue coagulation energy has been discontinued, either at the end of the pre-programmed period or based on the sensed completion of the lesion, in order to determine whether a transmural lesion has been formed. Without moving ablation and monitoring assembly 300, stimulation energy pulses may be supplied by stimulation electrodes to the tissue in the current path. The adjacent tissue can be monitored, either visually or with the ECG, to determine whether the adjacent tissue can be stimulated. If not, the physician may assume that a transmural lesion has been formed. In those instances where the lesion is incomplete, one or more stimulation electrodes may be used to determine where the gap, or the portion of the lesion that is not transmural, is located. Additional coagulation energy may then be supplied as necessary or desired to complete the lesion. It may be the case that the entire lesion is not transmural, which may require the coagulation procedure to be at least partially repeated.

Stimulation electrodes 310 can be relatively small, solid, low profile devices. For example, a stimulation electrode can be configured to be small enough that it does not form transmural myocardial lesions. Suitable surface are sizes can be about 0.2 mm$^2$ to about 10 mm$^2$, and suitable thicknesses can be about 0.01 mm to 0.5 mm. For example, a stimulation electrode can have a surface area of about 1 mm$^2$ and a thickness of about 0.1 mm. Suitable materials include platinum, platinum iridium, stainless steel, gold, silver-silver chloride or other non-toxic metals. Stimulation electrodes may also be formed by coating a conductive material onto variable spacing structures 330 or another underlying structure using conventional coating techniques or an ion beam-assisted deposition (IBAD) process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed in place. With respect to assembly, signal wire 312 may be welded or soldered to solid stimulation electrode 310 prior to assembly, while coated/printed electrodes may be formed onto the ends of signal wires that are already in place.

Exemplary tissue treatment systems and methods can involve providing monopolar stimulation pulses from stimulation electrodes 310. For example, a monopolar stimulation pulse can be generated by a pair of stimulation electrodes 310 which may be associated with one or more coagulation electrodes 320 that form the lesion. Stimulation electrode pairs may be used to supply pulses of stimulation energy to the tissue in the current path CP associated with one of the coagulation electrodes. The physician can monitor the adjacent tissue in the tissue structure, either visually or with an ECG, to determine whether that tissue was stimulated. This process may be sequentially repeated with the other stimulation electrode pairs in order to insure proper tissue contact with the applicable portions of the ablation and monitoring assembly 300. Thereafter, and without moving ablation and monitoring assembly 300, tissue coagulation energy may be applied to the tissue in the current path CP with the coagulation electrodes to form a lesion. Stimulation electrodes 310 may also be used to determine lesion depth and, correspondingly, whether or not a lesion is transmural at various points along the length of the lesion. Stimulation energy may be used to determine lesion depth because non-viable tissue, for example coagulated tissue, may not be stimulatable and may not propagate stimulation energy to nearby tissue. As such, when the application of stimulation energy that should stimulate tissue at a known depth fails to do so, and that depth is greater than or equal to the thickness of the body structure, it may be inferred that a transmural lesion has been formed. In some cases, the stimulation electrodes can be used on a coagulation electrode-by-coagulation electrode basis both during and before the coagulation process in the manner described above.

In the context of lesions formed within the heart, for example, localized current densities of at least about 2 mA/cm$^2$ may be needed to stimulate heart tissue. With respect to current transmitted from an electrode to tissue, the current density can be about $I/2\pi r^2$, where r is the distance from the electrode. Thus, a 1 mA stimulation pulse will typically stimulate viable tissue that is up to about 2.8 mm from the electrode, a 2 mA stimulation pulse will typically stimulate viable tissue that is up to about 4.0 mm from the electrode, a 10 mA stimulation pulse will typically stimulate viable tissue that is up to about 9.0 mm from the electrode, and a 20 mA stimulation pulse will typically stimulate viable tissue that is up to about 13.0 mm from the electrode. The left atrium is, for example, about 3 mm thick and accordingly, failure to stimulate with a 2 mA stimulation pulse indicates that a transmural lesion has been formed in the vicinity of the stimulation electrode. As noted above, these values can be substantially increased, for example by a factor of five, when the stimulation pulses are being supplied at the same time as the coagulation energy.

As shown in FIG. 3, stimulation electrodes 310 can be positioned between the coagulation electrodes 320 and target tissue. As such, the stimulation electrodes 310 can be in the current path of each coagulation electrode 320. Optionally, stimulation electrodes can be disposed between the current paths associated with coagulation electrodes 320.

FIGS. 4 and 5 illustrate aspects of an ablation and monitoring assembly 400 according to embodiments of the present invention. In addition to forming lesions, ablation and monitoring assembly 400 may also be used to determine whether or not therapeutic lesions have been properly formed by, for example, supplying tissue stimulation energy on one side of a lesion. The tissue on the other side of the lesion may then be monitored to determine whether an excitation block, typically the result of a continuous transmural lesion, has been formed in the target tissue. Tissue stimulation energy may also be used to determine lesion depth, which in turn, allows the physician to determine whether or not a lesion is transmural. In the exemplary implementations, the tissue stimulation energy is provided by ablation and monitoring assembly 400 that is capable of providing a pulse of energy that stimulates, but does not coagulate, tissue. An exemplary ablation and monitoring assembly 400 may be coupled with a conventional pacing apparatus, such as an external pulse generator. An ECG machine that is capable of monitoring and recording electrical impulses sensed by electrodes may also be in connectivity with ablation and monitoring assembly 400.

With respect to the stimulation energy, the power delivered to tissue for stimulation purposes will typically be significantly less than that which would form a transmural or otherwise therapeutic lesion in tissue. Stimulation electrodes may also be used for sensing. An exemplary stimulation energy delivery can include two stimulation pulses per second, each pulse being 1 millisecond long or wide. In some cases, a maximum amplitude can be 20 mA, which can create 10 V, for a total power delivery of 400 μW. Another exemplary stimulation energy delivery can include of two stimulation pulses per second, each pulse being 1 millisecond long or wide. In some cases, a maximum amplitude can be 10 mA, which can create 5 V, for a total power delivery of 100 μW. The amount of power required to coagulate tissue may in some instances range from 5 to about 150 W.

Ablation and monitoring assembly 400 can be in connectivity with a pacing apparatus or an EP recording apparatus via any suitable mechanisms. In some cases, a tissue treatment system can be configured so that coagulation electrodes will only receive coagulation energy and stimulation electrodes will only receive stimulation energy. The functionality of a tissue stimulation apparatus and EP recording apparatus may be combined into a single device. An EP recording apparatus may be configured to display measured conduction delays. Optionally, an EP recording apparatus may be used to store expected propagation delays for various tissue types and suction device configurations, including the positioning of the stimulation and sensing electrodes. An EP recording apparatus can compare the expected propagation delay (e.g. 10 ms) with no block to the measured propagation delay (e.g. 50 ms) and determine whether or not a complete conduction block has been formed. An EP recording apparatus can then provide an audible or visual indication concerning the status of the lesion. Alternatively conduction block can be determined by comparing a pre-treatment conduction delay, for example 20 ms, to a conduction delay during or following ablation. An increased conduction delay of more that a predetermined value for example 30 ms indicates a successful ablation attempt at the site. In the above example a conduction delay of 50 ms or more would indicate ablation success.

Embodiments of the present invention may be used to test the effectiveness of a lesion in any of a variety of ways. For example, after the lesion is formed, the physician may use the same surgical device that was used to form the lesion, such as a tissue treatment system that includes ablation and monitoring assembly 400, to perform a lesion evaluation. Stimulation electrodes that are provided on ablation and monitoring assembly 400 may be used to stimulate tissue on one side of a lesion by pacing at a higher rate than normal, for example 120 beats/minute. The local activation, if any, on the other side of the lesion can indicate whether or not the excitation block is incomplete. The stimulation electrodes may also be used to sense tissue within an isolated tissue region around which a lesion has been formed. Local activation within the isolated region from the heart's natural stimulation is indicative of a gap in the lesion. Additionally, the stimulation electrodes may be used to determine lesion depth. The placement of tissue stimulation electrodes on the same surgical device as the tissue coagulation electrodes can allow the physician to quickly and easily evaluate a lesion after it has been formed.

Ablation and monitoring assembly 400 can include a suction device 404, longitudinally extending bipolar pairs of tissue stimulation electrodes 426, and longitudinally extending bipolar pairs of sensing electrodes 428 near the lateral edges of the suction device. A plurality of bipolar pairs of stimulation electrodes 426 can extend along a length of one side of the suction device 404, and a plurality of bipolar pairs of sensing electrodes 428 can extend along a length of the other side of the suction device. Each bipolar pair can be adjacent to one of the suction ports 410, 414 and, accordingly, the electrodes can be held firmly against tissue when suction force is applied. Stimulation electrodes 426 can be located on one side of a slot 420 and sensing electrodes 428 can be located on the other side. As such, the tissue stimulation and sensing electrodes 426 and 428 can be on opposite sides of ablation and monitoring assembly 400, on opposite sides of coagulation electrodes 110, and on opposite sides of a lesion formed by the coagulation electrodes.

Embodiments of the present invention encompass a wide variety of alternative stimulation and sensing electrode schemes. By way of example, but not limitation, the number of bipolar pairs of tissue stimulation and sensing electrodes 426 and 428 may range from a large number of pairs, as shown, to a single pair tissue stimulation electrodes and a single pair sensing electrodes. The single pairs may be located near the middle, measured longitudinally, of suction device 404. Another alternative is unipolar stimulation and sensing. Here, single stimulation electrodes, as opposed to a bipolar pair, may be positioned adjacent to each of the suction ports 410 on one side of the suction device 404 and single sensing electrodes may be positioned adjacent to each of the suction ports on the other side of the suction device.

With respect to configuration and manufacture, the exemplary tissue stimulation and sensing electrodes 426 and 428 may be relatively small, low profile devices. For example, the electrodes may be too small to form transmural myocardial lesions. Suitable sizes may be about 0.5 mm to 1 mm in diameter, and a suitable thickness may be about 0.01 mm. Such electrodes may be formed by coating a conductive material onto the suction device 404 using conventional coating techniques or an IBAD process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed onto the suction device 404. A stimulation electrode can be connected with a signal wire or line. In some cases, a signal lines may be very thin (e.g. about 40-50 gauge wire).

An exemplary tissue treatment system may be used to test the quality of lesions formed during a lesion formation procedure in a variety of ways. For example, a suction source may be used to maintain the position of the suction device 404 after power transmission from the coagulation electrodes 110 has ended. A pulse of stimulation energy, for example about 10 mA, may be applied to viable tissue on one side of the lesion by a pair of stimulation electrodes 426*a*. The viable tissue on the other side of the lesion may be monitored with a pair of sensing electrodes 428*a* to detect the local excitation from the pulse of stimulation energy. Ablation and monitoring assembly 400 can be used to measure the amount of time between the delivery of the pulse to the tissue by the stimulation electrode pair 426*a* and the detection of the local activation by the sensing electrode pair 428*a* on the other side of the lesion. The conduction delay, or amount of time that between pulse delivery on one side of the lesion and local activation on the other can be indicative of the quality or extent of the lesion.

In the context of the formation of lesions within the heart, the conduction delay from the stimulation electrode pair 426*a* and the sensing electrode pair 428*a* will typically be about 10 ms when the distance between the pairs is about 1 cm, absent a conduction block. Here, the excitation pulse may travel a relatively short distance. Conversely, when a complete conduction block is formed between the stimulation and sensing pairs, the excitation pulse may be forced to travel around the lesion. The longer travel distance can result in a longer conduction delay, which is indicative of the formation of a therapeutic lesion. For example, a continuous 50 cm transmural lesion that creates a complete conduction block along its length will typical increase the conduction delay to about 50 ms.

In some embodiments, a lesion can be tested at various points along its length, one point at a time. The lesion may be tested with each of the stimulation and sensing electrode pairs that are adjacent to a coagulation electrode that was used to form a lesion. If for example, the proximal four coagulation electrodes are used to form a lesion, then the proximal four pairs of stimulation and sensing electrodes will be used, one stimulation/sensing at a time, to determine whether or not the lesion creating procedure created a complete conduction block. In some cases, if a pacing pulse is able to cross the lesion, the heart will beat faster, for example 120 beats/minute. This may be determined by observation or by use of an ECG machine that is monitoring the heart. Additional coagulation may be used to complete an incomplete lesion. Because muscle bundles are not always connected near the pulmonary veins, it may be desirable to apply stimulation energy to a number of tissue areas to reduce the possibility of false negatives. Stimulation electrodes may be used to monitor tissue within a region that was intended to be isolated. In the context of pulmonary vein isolation, for example, stimulation electrodes may be placed in contact with viable tissue on the pulmonary vein side of the lesion. Local activation within the isolated region from the heart's natural stimulation is indicative of a gap in the lesion. Ablation and monitoring assembly 400 may be used to determine whether or not a lesion is transmural. Tissue stimulation electrodes may be connected to a tissue stimulation apparatus and used to provide stimulation energy. Tissue stimulation electrodes may also be used for sensing local tissue activation. Stimulation electrodes may operate in a bipolar mode, and also may operate in unipolar mode.

In some tissue treatment system or method embodiments, coagulation electrodes can be configured to transmit RF energy. Optionally, other types of coagulation elements, such as such as lumens for chemical ablation, laser arrays, ultrasonic transducers, microwave electrodes, ohmically heated hot wires, and the like may be substituted for or supplement the coagulation electrodes. Coagulation electrodes may be arranged as a series of spaced electrodes. Optionally, a single elongate coagulation electrode may be employed. Coagulation electrodes can be in the form of wound, spiral closed coils. The coils can be made of electrically conducting material, such as copper alloy, platinum, or stainless steel, or compositions such as drawn-filled tubing, for example a copper core with a platinum jacket. The electrically conducting material of the coils can be further coated with platinum-iridium or gold to improve its conduction properties and biocompatibility.

In the case of laser ablation, some versions include an end firing diode that can be automatically moved so as to direct energy toward several distinct locations along a line or path. In some versions, a laser beam is transmitted down a control diffracting mechanism, and reflected along a direction orthogonal to the longitudinal axis of the device. Hence, light can be dispersed in a uniform fashion along the diffracting mechanism. Laser ablation techniques according to embodiments of the present invention can involve these types of laser approaches, as well as related techniques which are described in U.S. Pat. Nos. 6,071,302 and 6,270,492, the contents of which are incorporated herein by reference.

Optionally, coagulation electrodes 110 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The coagulation electrodes can also be in the form of helical ribbons. The electrodes can also be formed with a conductive ink compound that is pad printed onto a non-conductive tubular body. A conductive ink compound can include a silver-based flexible adhesive conductive ink (polyurethane binder), however other metal-based adhesive conductive inks such as platinum-based, gold-based, copper-based, etc., may also be used to form electrodes. Such inks may be more flexible than epoxy-based inks. Open coil electrodes may also be employed for coagulation.

Exemplary flexible coagulation electrodes 110 can be about 4 mm to about 20 mm in length. In some embodiments, the electrodes are about 12.5 mm in length with about 1 mm to about 3 mm spacing, which can result in the creation of continuous lesion patterns in tissue when coagulation energy is applied simultaneously from adjacent electrodes through tissue to an indifferent electrode. For rigid coagulation electrodes, the length of the each electrode can vary from about 2 mm to about 10 mm. The diameter, whether flexible or rigid, will typically be about 3 mm. For cardiovascular applications, the length will sometimes range from between about 2 cm and 8 cm in those instances where power is supplied at both longitudinal ends of each electrode, and the end to end resistance is about 5 ohm to about 15 ohm. The diameter of the electrodes may in some cases range from about 1.5 mm to about 3 mm for cardiovascular applications and, in some embodiments, the outer diameter is about 2 mm.

A tissue treatment system may include one or more temperature sensors which can help provide temperature readings and facilitate improved temperature control. As such, the actual tissue temperature can correspond to the temperature set by the physician on the power supply and control device, thereby providing the physician with control of the lesion creation process and reducing the likelihood that embolic materials will be formed. A reference thermocouple may also be provided.

A power supply and control system can include an electrosurgical unit (ESU) that supplies and controls RF power. An ESU can be is capable of supplying and controlling power on an electrode-by-electrode basis, in a "multi-channel control." An ESU can transmit energy to the coagulation electrodes and receives signal from the temperature sensors via any suitable connectivity. An ESU can be operable in a bipolar mode, where tissue coagulation energy emitted by one of the coagulation electrodes is returned through one of the other coagulation electrodes, and a unipolar mode, where the tissue coagulation energy emitted by the coagulation electrodes is returned through one or more indifferent electrodes that are externally attached to the skin of the patient with a patch, or one or more electrodes that are positioned in the blood pool, and a cable. It is also possible to supply power in a combined bipolar/unipolar mode. An ESU can individually power and control each coagulation electrode 110, optionally based on the hottest of the two measured temperatures at that particular electrode.

Embodiments of the present invention encompass tissue treatment systems and methods for verifying electrical conduction block across ablation lesions and for verifying the effectiveness of an ablation procedure in creating an electrical conduction block across the cardiac tissue. An exemplary verification system includes a conduction block-verification mechanism such as a pacing probe or electrode. A verification method can involve transmitting an electrical pulse to a patient tissue so as to stimulate the tissue. In some cases, the electrical pulse is applied at a rate higher than the intrinsic atrial or ventricular contraction rate or heart rate. A measurement of the pacing threshold, or the minimum voltage or amperage required to excite the tissue, above the intrinsic excitation rate, can be recorded or monitored prior to, during, and following completion of one or more ablation lesions, which may be aimed to isolate specific regions of the heart.

In use, a tissue treatment system can be used to directly contact the epicardium of the heart and transmits electrical energy to electrically stimulate the heart. Such electrical energy can be delivered by a pulse generator that is coupled with or integral to the tissue treatment system. In some cases, an operator can position the tissue treatment system using direct or endoscopic visualization of the tissue surface. Optionally, an operator can monitor, verify, or evaluate a conduction block with the assistance of an ECG recorders. A tissue treatment system can be configured to transmit electrical pacing pulses of variable amplitude up to 20 mA or 10 V in amplitude to pace the heart above normal sinus rhythm, optionally up to 200 BPM to the target anatomical area of the epicardium. A tissue treatment system may also be capable of passively transmitting electrical pulses from the heart to an ECG recorder.

A tissue treatment method may include the temporary pacing of a portion of the heart, for example the left atrium, and the verification or evaluation of an electrical conduction block across one or more ablation lesions. Such methods can provide an indication of lesion continuity and electrical isolation of one or more specific regions on the heart. A tissue treatment system can be used after creating a set of lesions on the epicardium of the left atrium encircling the pulmonary veins in conjunction with surgical, interventional cardiology, or electrophysiology treatments for atrial fibrillation to determine if or to what extent electrical conduction block is achieved.

A tissue treatment system can be used to pace the left atrium by contacting the left atrium both inside and outside an encircling lesion around the pulmonary veins. If significantly more voltage or current is required to pace the heart from inside the encircling lesion as opposed to outside, an inference of electrical isolation of the pulmonary veins can be made. Exemplary methods can be used to assess electrical isolation of several regions of the heart across ablation lesions during surgical treatment of atrial fibrillation, open or minimally invasively, epicardially or endocardially. A pulse generator can supply a higher than normal pacing rate and electrical impulse at variable amplitudes. The tissue treatment system can be used to contact the left atrium within the encircling lesion adjacent to the pulmonary veins and paced to determine if electrical isolation or block was successful. If block is not successful, then the impulse may be captured outside the encircling lesion and pacing of the entire heart may take place.

Embodiments of the present invention encompass tissue treatment systems and methods that provide for the selective activation and deactivation of one or more stimulation or pacing electrodes, optionally based on an evaluation of the conduction block status of a patient tissue. Embodiments also encompass methods that involve determining or identifying a set of one or more stimulation or pacing electrodes for activation. Relatedly, embodiments also encompass methods that involve determining or identifying a set of one or more coagulation electrodes for activation. In some cases, tissue treatment systems can be configured to activate one or more stimulation electrodes or coagulation electrodes based on a determination of whether an ablation and monitoring assembly of the tissue treatment system is in appropriate contact with the patient tissue. Relatedly, tissue treatment systems can be configured to modulate the amount of energy transmitted by one or more stimulation electrodes or coagulation electrodes based on a determination of whether an ablation and monitoring assembly of the tissue treatment system is in appropriate contact with the patient tissue. In some cases, tissue treatment systems can be configured to activate one or more stimulation electrodes or coagulation electrodes based on a determination or evaluation of the conduction block status of a patient tissue. For example, a method may involve activating a coagulation electrode which is disposed at or near tissue not having a conduction block, and deactivating or not activating a coagulation electrode which is disposed at or near tissue that has a conduction block. Optionally, tissue treatment systems can be configured to modulate the amount of energy transmitted by one or more stimulation electrodes or coagulation electrodes based on a determination or evaluation of the conduction block status of a patient tissue. Relatedly, a tissue treatment system can be configured to activate or deactivate one or more stimulation electrodes or coagulation electrodes based on a determination or evaluation of whether an ablation and monitoring assembly of the tissue treatment system is in appropriate contact with the patient tissue and a determination or evaluation of the conduction block status of a patient tissue. A tissue treatment system can also be configured to modulate the amount of energy transmitted by one or more stimulation electrodes or coagulation electrodes based on a determination or evaluation of whether an ablation and monitoring assembly of the tissue treatment system is in appropriate contact with the patient tissue and a determination or evaluation of the conduction block status of a patient tissue.

According to some embodiments, tissue treatment system can be configured to perform a conduction block test or evaluation during a coagulation or RF procedure, and to modulate the amount of coagulation or ablation energy that is applied by the system to the patient's tissue. For example, a tissue treatment system can be configured to determine when or where to initiate, increase, stop, or reduce power to one or more coagulation electrodes of an ablation and monitoring assembly based on a conduction block analysis. Similarly, a tissue treatment system can be configured to control when or where and in what amount energy is applied via one or more coagulation electrodes of an ablation and monitoring assembly based on a conduction block analysis. Often, such methods can involve determining when to stop at least a portion of an ablation treatment. Relatedly, methods can involve stimulating a patient tissue to determine where a conduction block has been established, or at least partially established.

In some embodiments, a tissue treatment system can include or be in connectivity with a coagulation energy generator, such as an RF energy generator, which may include an integrated control mechanism for modulating the output of the generator based on the conduction block status of a patient tissue. In some cases, a tissue treatment system includes an ablation and monitoring assembly that is configured to apply a pacing or stimulation energy to the tissue via one or more coagulation electrodes. Standard ablation or coagulation electrodes are typically larger than standard stimulation electrodes, because ablation electrodes usually deliver greater amounts of current. Hence, stimulation of tissue with an ablation electrode involves the application of more current than would otherwise be applied with a stimulation electrode. Generally, stimulation of tissue is initiated by a particular current density in the tissue. Due to current dissipation in the tissue, as the surface area of an electrode is increased there is a corresponding proportional increase in the current to the electrode for stimulation. If there is a ten fold increase in the electrode surface area, a ten fold increase in the current amplitude is needed to achieve the current density required for tissue stimulation (the voltage remains substantially unchanged). In many cases, the application of about 2 to 10 volts through an electrode is sufficient to stimulate a tissue independent of electrode size, but the required current is greater for larger electrodes.

In some embodiments, a coagulation electrode that is used to deliver stimulation energy can be configured to output 100 to 200 milliamps, while maintaining a compliance of 10 to 20 volts. In some cases, an RF electrode can be configured to deliver energy at 460 kHz, which may require a pacing circuit having a blocked return path. A two stage LC circuit can be used for passive stimulation. Relatedly, a tissue treatment system can have a first circuit for pacing and a second circuit for ablation, where the first and second circuits are isolated from one another. In some cases, an LC circuit can be configured with a low impedance path at low frequencies used for pacing and a high impedance at ablation frequencies.

Embodiments of the present invention also encompass a tissue treatment system having an integrated ESU with a user interface that provides output signifying the status of one or more lesions. For example, a user interface can identify or show where ablation is successful or where there is a gap in a linear lesion. Relatedly, a user interface can show electrodes or otherwise provide a representation of one or more electrodes and their positioning at or near patient tissue. In some cases, a user interface can reconstruct a model of the heart to identify areas of successful and unsuccessful ablation. Where a touch screen is used, the operator can touch the screen to identify where additional ablation attempts should be done.

An exemplary treatment method can include applying a first ablative energy to a first tissue location via a first electrode, and applying a second ablative energy to a second tissue location via a second electrode. The method can also include performing a detection or monitoring step before, during, or after applying the first and second ablative energies. The method can include detecting a subthreshold electrical conductivity for the first tissue location and a threshold electrical conductivity for the second tissue location, and discontinuing or diminishing application of the first ablative energy to the first tissue location while continuing application of the second ablative energy to the second tissue location. In a related embodiment, an exemplary treatment method includes activating one or more coagulation electrodes of an ablation and monitoring assembly, applying energy to a patient tissue with the activated coagulation electrodes, performing a conduction block or lesion pattern analysis of the patient tissue, and adjusting the activation level of one or more of the coagulation electrodes based on the conduction block or lesion pattern analysis.

Embodiments also encompass selective deactivation methods using a tissue treatment system. For example, a tissue treatment method can involve activating one or more coagulation electrodes of an ablation and monitoring assembly, continuing application of a first ablative energy to a first tissue location via a first ablation electrode, and discontinuing or reducing application of a second ablative energy to a second tissue location via a second ablation electrode after detecting a conduction block at or near the second tissue location. Similar embodiments involve operating an ablation and monitoring assembly during a cardiac surgical procedure, evaluating a conduction block condition at a first tissue location, and discontinuing application of a first ablative energy to the first tissue location in response to the condition of the conduction block at the first tissue location, and continuing application of the second ablative energy to the second tissue location, optionally in response to a conduction block status of the second tissue location. Further, exemplary methods can involve operating an ablation assembly during a cardiac surgical procedure, evaluating a conduction block condition of a patient tissue treatment site, and based on the evaluation of the conduction block condition, continuing application of a first ablative energy to a first tissue location, and discontinuing or reducing application of a second ablative energy to a second tissue location.

Figure 6:
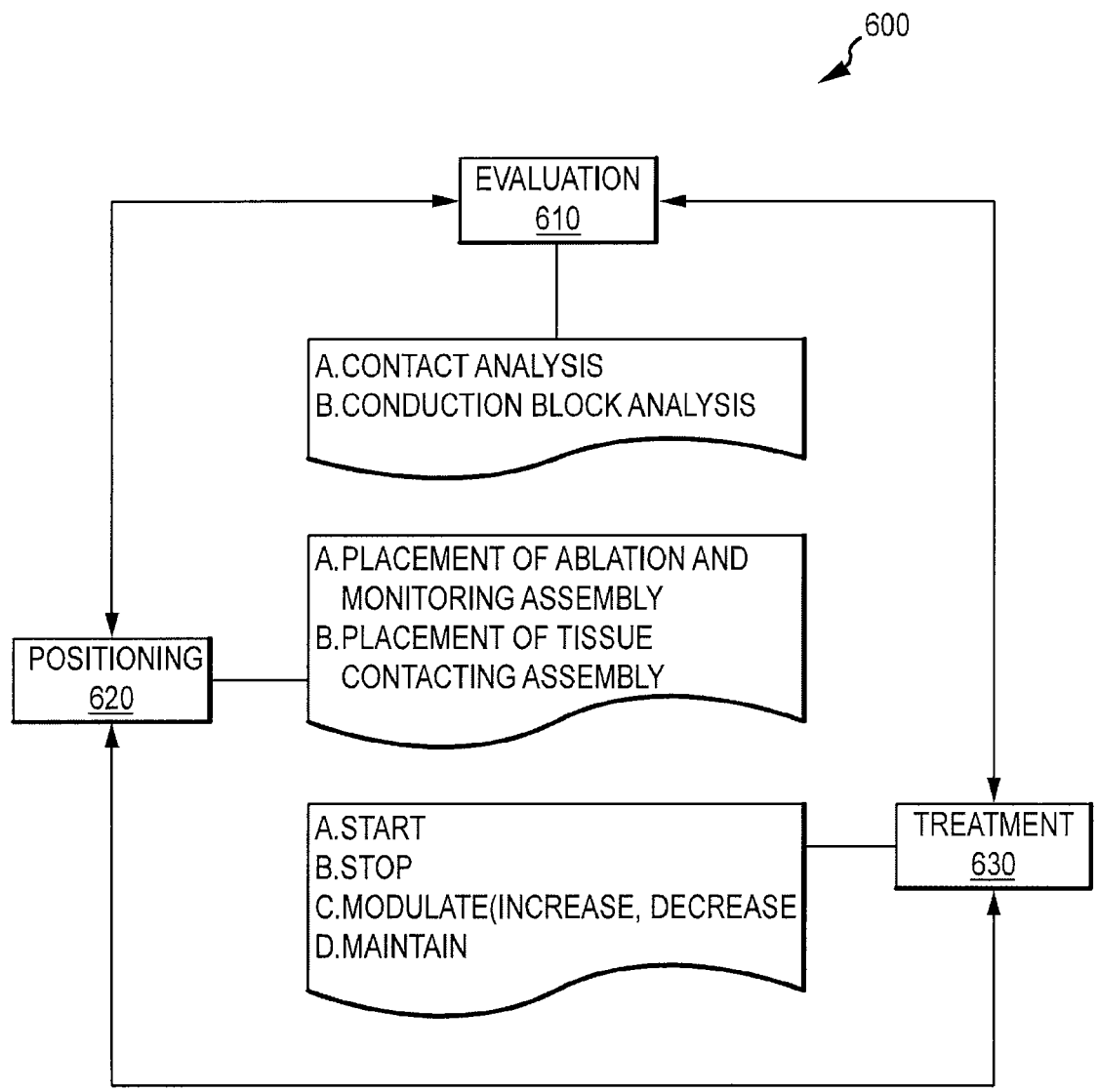
FIG. 6 illustrates aspects of medical methods according to embodiments of the present invention.

FIG. 6 illustrates aspects of exemplary medical methods 600 according to embodiments of the present invention. As shown here, medical method 600 can include an evaluation step 610, a positioning step 620, and a treatment step 630. A method may include one or more of such steps, in any desired combination, sequence, or permutation. In some embodiments, one or more steps can be performed simultaneously or substantially simultaneously. For example, a method may include a treatment step 630, followed by a positioning step 620, followed by a simultaneous evaluation step 610 and treatment step 630.

Evaluation step 610 can include determining which portions of a tissue treatment system may be in contact with patient tissue. For example, evaluation step 610 can include determining which portion or portions of an ablation and monitoring assembly may be in contact with patient tissue. Optionally, evaluation step 610 can include determining which portion or portions of a tissue contacting assembly may be in contact with patient tissue. In some cases, evaluation step 610 can include determining the conduction block status of one or more locations of patient tissue. Evaluation step 610 often provides information which can be used by an operator or surgeon to determine the efficacy of a positioning step or a treatment step. Evaluation step 610 can also provide information which can be used to determine whether to maintain, adjust, or discontinue aspects of a positioning step or treatment step.

Positioning step 620 can include placing, positioning, or repositioning one or more portions or elements of an ablation and monitoring assembly, such as one or more stimulation electrodes or one or more coagulation electrodes, at or near any desired location of patient tissue. Similarly, positioning step 620 can include placing, positioning, or repositioning one or more portions or elements of a tissue contacting assembly of at or near any desired location of patient tissue.

Treatment step 630 can involve the application of treatment to patient tissue. In some cases, treatment step 630 encompasses aspects of the application of a coagulation or ablation treatment to patient tissue. For example, treatment step 630 can include the initiation of energy through one or more coagulation electrodes to patient tissue. Treatment step 630 may include the cessation of energy through one or more coagulation electrodes. In some cases, treatment step 630 includes the modulation of energy, such as an increase or decrease of energy, through one or more coagulation electrodes.

Figure 7:
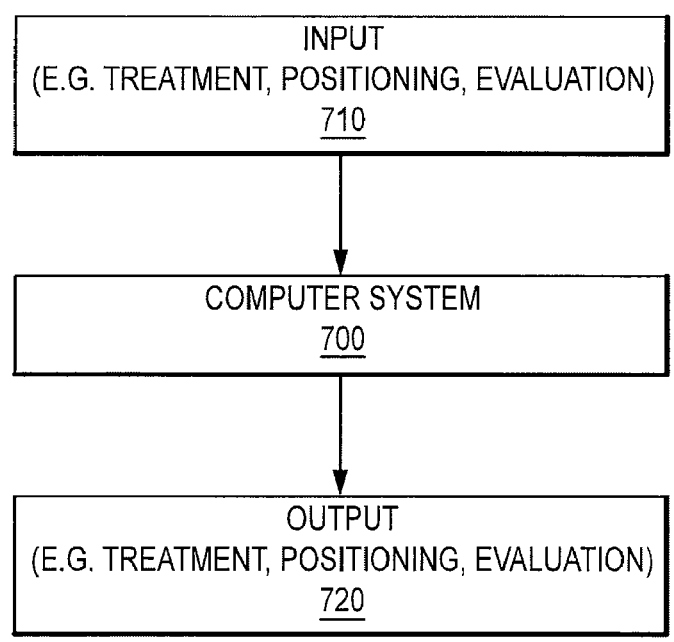
FIG. 7 shows aspects of a computer system according to embodiments of the present invention.

FIG. 7 shows aspects of an exemplary computer system 700 according to embodiments of the present invention. Computer system 700 can include one or more modules configured to receive input 710 such as treatment information, positioning information, or evaluation information. Input information or signals can be provided by a tissue treatment system or by a user such as a surgeon or other personnel involved with a medical procedure. Computer system 700 can also include one or more modules configured to transmit output 720 such as treatment information, positioning information, or evaluation information. Output information or signals can be provided to a tissue treatment system or to a user such as a surgeon or other personnel involved with a medical procedure. Computer system 700 can be configured to process aspects of medical methods, such as those described in connection with the medical methods depicted in FIG. 6. In some embodiments, computer system 700 in integrated into a tissue treatment system. In some embodiments, computer system 700 is separate from, but in communicable connectivity with, a tissue treatment system. For example, computer system 700 may be connected with a tissue treatment system via a data transmission cable. In some cases, computer system 700 can be in wireless communication with a tissue treatment system.

Figure 7A:
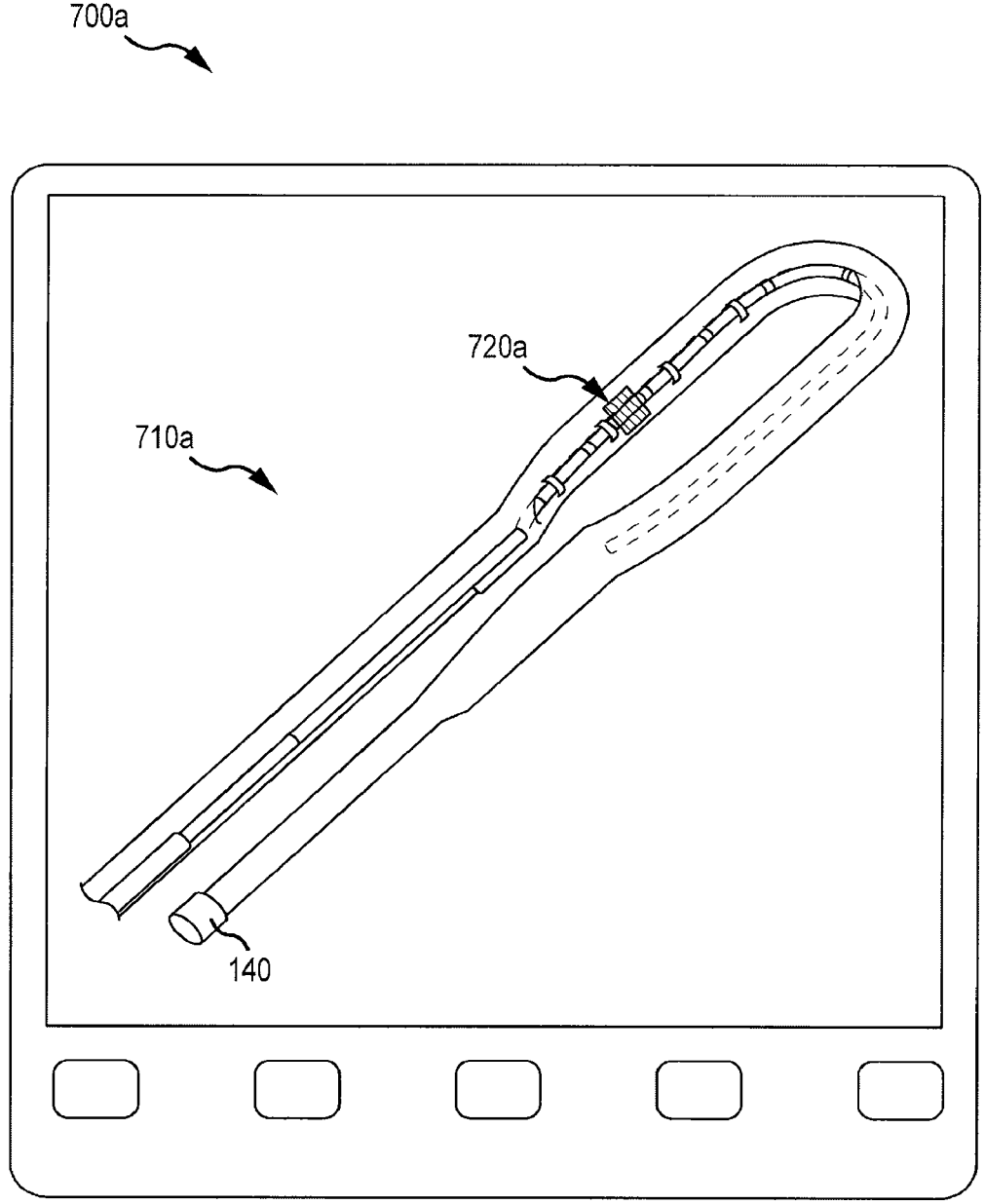
FIG. 7A illustrates a graphical output of a user interface according to embodiments of the present invention.

A tissue treatment system can have an input for receiving instructions or commands, such as initial set up instructions. The input can be incorporated into a touch screen or other user interface. In some cases, a user interface can be configured to receive input and also display output. For example, a user interface can be configured to switch between an input mode and an output mode. Hence, an operator can view output on a user interface display screen when it is in an output mode, and can also input data or instructions on the same screen when it is in an input mode. Tissue treatment systems can be configured to display or output information that is gleaned as a result of pacing or stimulation procedures. A user interface can provide a graphical illustration or presentation of which electrodes or ablation elements, or portions thereof, correspond to tissue having a conduction block. A user interface can also provide a graphical presentation of the status of a lesion before, during, or after an ablation treatment. In some cases, a user interface provides a real time display of the status of a lesion as it is formed by an ablation procedure. FIG. 7A provides an exemplary graphical output of a user interface 700a. As shown here, an image 710a of an ablation mechanism is displayed on the interface. Image 710a can indicate instances where breaks or gaps in a lesion are present. For example, if there is a gap in a lesion at or near a particular electrode of the ablation mechanism, image 710a can include provide a marker 720a corresponding to that electrode. The marker may be, for example, a highlighted image, a blinking image, a colored image, or the like. Hence, an image can be displayed to a user or operator showing which electrode or electrodes correspond to a gap in the lesion. The electrodes may be blinked, highlighted, colored, or the like. In some cases, a linear array of electrodes may be presented in an image, and the electrodes identified as corresponding to a gap can be marked. It is understood that such markings can be displayed in real time during an ablation procedure. In some embodiments, a first type of marking can be shown corresponding to regions or locations where a lesion gap occurs, and a second type of marking can be shown corresponding to regions or locations where a lesion occurs. Hence, a display may show a blue marker where a lesion gap occurs, and a red marker where a lesion occurs, for example. Optionally, a marking can be shown where a lesion occurs, and no marking shown where a gap occurs, or vice versa.

Figure 8:
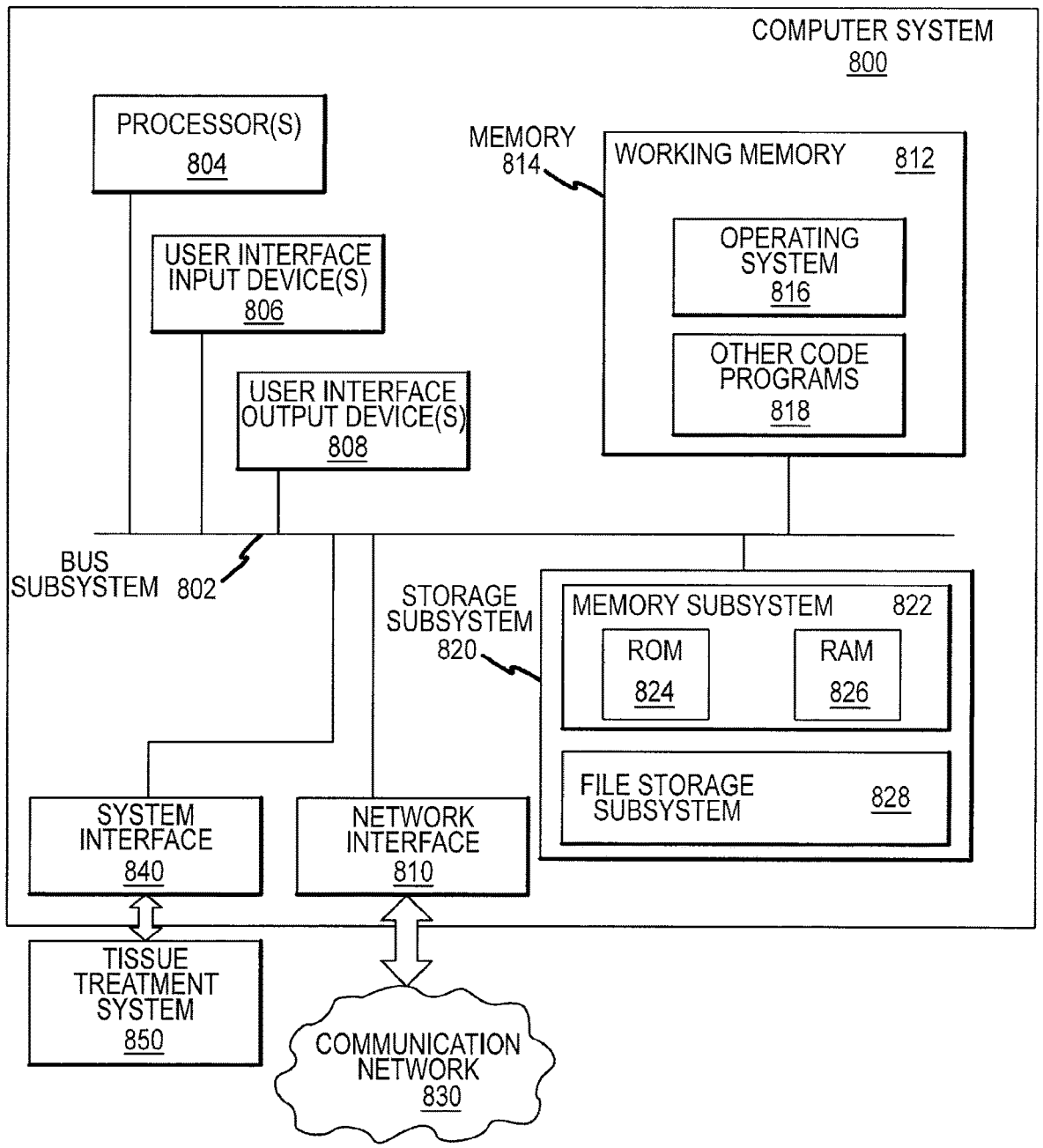
FIG. 8 provides a block diagram of a computer system according to embodiments of the present invention.

FIG. 8 is a simplified block diagram of an exemplary computer system 800 that broadly illustrates how individual system elements or aspects of a tissue treatment computer system may be implemented in a separated or more integrated manner. Computer system 800 is shown comprised of hardware elements that are electrically coupled via a bus subsystem 802, including one or more processors 804, one or more input devices 806 such as user interface input devices, one or more output devices 808 such as user interface output devices, and a network interface 810.

In some embodiments computer system 800 also comprises software elements, shown as being currently located within working memory 812 of memory 814, including an operating system 816 and other code 818, such as a program designed to implement method embodiments of the present invention.

Likewise, in some embodiments computer system 800 may also include a storage subsystem 820 that can store the basic programming and data constructs that provide the functionality of the various embodiments of the present invention. For example, software modules implementing the functionality of the methods of the present invention, as described herein, may be stored in storage subsystem 820. These software modules are generally executed by the one or more processors 804. In a distributed environment, the software modules may be stored on a plurality of computer systems and executed by processors of the plurality of computer systems. Storage subsystem 820 can include memory subsystem 822 and file storage subsystem 828. Memory subsystem 822 may include a number of memories including a main random access memory (RAM) 826 for storage of instructions and data during program execution and a read only memory (ROM) 824 in which fixed instructions are stored. File storage subsystem 828 can provide persistent (non-volatile) storage for program and data files, and may include tangible storage media which may optionally embody patient, device, treatment, evaluation, positioning or other medical data. File storage subsystem 828 may include a hard disk drive, a floppy disk drive along with associated removable media, a Compact Digital Read Only Memory (CD-ROM) drive, an optical drive, DVD, CD-R, CD-RW, solid-state removable memory, other removable media cartridges or disks, and the like. One or more of the drives may be located at remote locations on other connected computers at other sites coupled to computer system 800. The modules implementing the functionality of embodiments of the present invention may be stored by file storage subsystem 828. In some embodiments, the software or code can provide protocol to allow the computer system 800 to communicate with communication network 830. Often such communications can include dial-up or internet connection communications, wireless communications, or any other desired or suitable connectivity.

It is appreciated that system 800 can be configured to carry out various method aspects of the present invention. For example, processor component or module 804 can be a microprocessor control module configured to receive data or signals from input device or module 806, and transmit data or signals to output device or module 808 and/or network interface device or module 810. Each of the devices or modules of the present invention can include software modules on a computer readable medium that is processed by a processor, hardware modules, or any combination thereof. Any of a variety of commonly used platforms, such as Windows, MacIntosh, and Unix, along with any of a variety of commonly used programming languages, such as C or C++, may be used to implement embodiments of the present invention. In some cases, tissue treatment systems include FDA validated operating systems or software/hardware modules suitable for use in medical devices. Tissue treatment systems can also include multiple operating systems. For example, a tissue treatment system can include a FDA validated operating system for safety critical operations performed by the treatment system, such as data input, power control, diagnostic procedures, recording, decision making, and the like. A tissue treatment system can also include a non-validated operating system for less critical operations.

User interface input devices 806 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 806 may also download a computer executable code from a tangible storage media or from communication network 830, the code embodying any of the methods of the present invention. It will be appreciated that terminal software may be updated from time to time and downloaded to the terminal as appropriate. In general, use of the term "input device" is intended to include a variety of conventional and proprietary devices and ways to input information into computer system 800.

User interface output devices 808 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 800 to a user. In some cases, a tissue treatment system can include an integrated user interface device, where features of user interface input device 806 are combined with features of user interface output device 808.

Bus subsystem 802 provides a mechanism for letting the various components and subsystems of computer system 800 communicate with each other as intended. The various subsystems and components of computer system 800 need not be at the same physical location but may be distributed at various locations within a distributed network. Although bus subsystem 802 is shown schematically as a single bus, alternate embodiments of the bus subsystem may utilize multiple busses.

Network interface 810 can provide an interface to an outside network 830 and/or other devices. Outside communication network 830 can be configured to effect communications as needed or desired with medical personnel, institutions, or other entities. It thus can receive an electronic packet from computer system 800 and transmits any information or signal as needed or desired back to computer system 800. In addition to providing such infrastructure communications links internal to the system, the communications network system 830 may also provide a connection to other networks such as the internet and may comprise a wired, wireless, modem, and/or other type of interfacing connection. As noted above, in some embodiments, a computer system can be in integrated into a tissue treatment system, and in some embodiments, a computer system can be separate from, but in connectivity with, a tissue treatment system. Hence, a computer system 800 can include a system interface 840 that provides an interface to a tissue treatment system 850.

It will be apparent to those skilled in the art that substantial variations may be used in accordance with any specific requirements. For example, customized hardware might also be used and/or particular elements might be implemented in hardware, software (including portable software, such as applets), or both. Further, connection to other computing devices such as network input/output devices may be employed. Computer terminal system 800 itself can be of varying types including a computer terminal, a personal computer, a portable computer, a workstation, a network computer, or any other data processing system. Due to the ever-changing nature of computers and networks, the description of computer system 800 depicted in FIG. 8 is intended only as a specific example for purposes of illustrating one or more embodiments of the present invention. Many other configurations of computer system 800 are possible having more or less components than the computer system depicted in FIG. 8. Relatedly, any of the hardware and software components discussed above can be integrated with or configured to interface with other medical treatment or information systems used at other locations.

Figure 9:
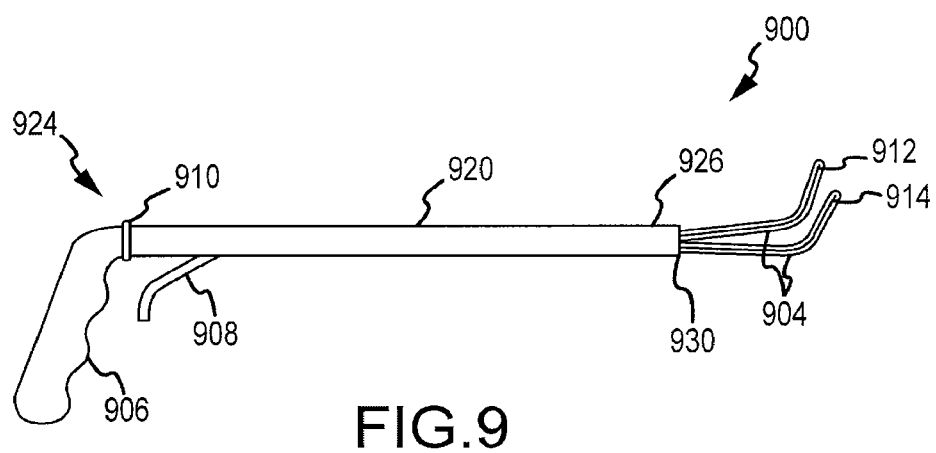
FIG. 9 depicts a tissue treatment system according to embodiments of the present invention.

Referring now to FIG. 9, another embodiment of ablation device or tissue treatment system 900 suitably includes at least one elongate shaft 902 having a proximal end 924 and a distal end 926, a jaw member or clamp 904 coupled with shaft 902 near distal end 926, at least one ablation member 912, 914 coupled with jaw or clamp member 904, and a handle 906 and at least one actuator 908, 910 near the proximal end 924 for manipulating device 900, opening and closing the jaw member, activating ablation member 912, 914 and the like. Device 900 is generally configured to be introduced through a minimally invasive sheath, trocar or incision, though it may also be used in open surgical procedures. Shaft 902 may be made of any suitable material, such as metal, ceramic, polymers or any combination thereof, and may be rigid along its entire length or rigid in parts and flexible in one or more parts. In various embodiments, the shaft may be malleable, may articulate about at least one joint and/or may be steerable for positioning the device. In some embodiments, the ablation member is coupled with a portion of the shaft.

Jaw member or clamp 904 may be disposed on or near distal end 926 of shaft 902 and is generally configured to open and close to grasp epicardial or other tissue between the opposing jaws. For example, jaw member 904 may be coupled with shaft 902 at a hinge point 930 to allow for such opening and closing motion. An ablation member is coupled with at least part of jaw member 904. As with embodiments described elsewhere herein, the ablation member may use any suitable energy source for ablating tissue. In some embodiments, multiple ablation members 912, 914 may be used. For example, one electrode 912 of a bipolar ablation member may be coupled with one opposing jaw and another electrode 914 may be coupled with the other opposing jaw. Alternatively, ablation members 912, 914 may include one unipolar ablation device or any of the ablation devices described with reference to various embodiments herein. The jaw member and/or the ablation member may be shaped to contact and ablate the epicardial tissue in a pattern such as, but not limited to, a U-shaped pattern, an L-shaped pattern, a circular pattern or a linear pattern. Actuators 908, 910 may have one or more various functions, such as opening and closing jaw member 904, activating ablation members 912, 914, changing an angle of orientation of jaw member 904, straightening or bending jaw member 904 and/or the like. One actuator 910, for example, may comprise a trigger-like actuator while another actuator 908 may comprise a turnable dial.

Generally, jaw or clamp member 904 may have any suitable configuration for contacting a surface of a heart, for grasping epicardial or other tissue to be ablated and/or for placing ablation members 912, 914 in contact with tissue to be ablated. As such, jaw or clamp members 904 may be straight, curved, bent or otherwise configured for contacting, grasping and/or ablating tissue.

Figure 9A:
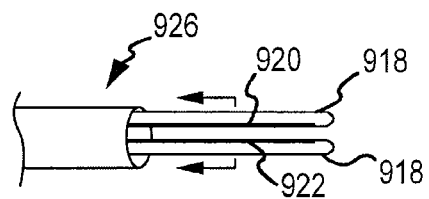
FIG. 9A illustrates straight jaw aspects of a tissue treatment system according to embodiments of the present invention.

In some embodiments, jaw member or clamp 904 may be adjustable via an actuator 908, 910, so as to allow their shapes to be bent, straightened or the like during a procedure. With reference to FIG. 9A, one embodiment of a straight jaw member or clamp 918 may allow jaw or clamp member 918 to be retracted within shaft (arrows). Retraction may help protect a patient as well as jaw member during insertion and advancement of the device within the patient. Ablation members 920, 922 on such straight jaw or clamp members 918 may be bipolar RF members, unipolar RF members or any other suitable ablation members or devices.

Optionally, the device may further include an insulation member at least partially surrounding the device to protect body structures in the vicinity of the epicardial tissue to be ablated from damage due to heat or electrical current. Also optionally, the ablation member may be adjustable to deliver two or more varying amounts of ablative energy to two or more locations on the epicardial tissue. Various embodiments may further include at least one sensor for sensing a quantity of ablation provided by the ablation member to the tissue.

Figure 10:
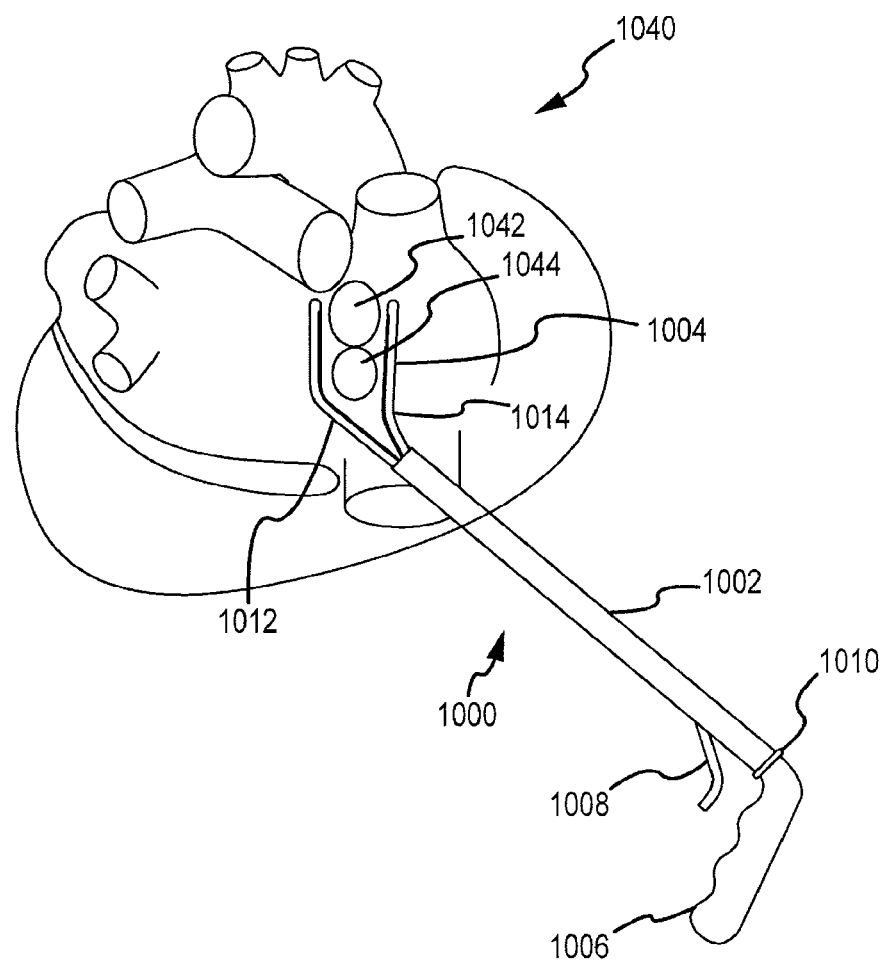
FIG. 10 depicts a tissue treatment system according to embodiments of the present invention.

FIG. 10 shows an exemplary ablation device or tissue treatment system 1000 in a position for performing an ablation procedure on epicardial tissue of heart 1040. Ablation device 1000 can ablate in a pattern approximating two lines adjacent the right pulmonary veins 1042, 1044. It should be understood that jaw member 1004 and ablation members 1012, 1014 could alternatively be configured in any other suitable shape, size or configuration to ablate in other patterns on heart 1040. Additionally, device 1000 may be moved to a variety of positions to ablate multiple patterns in multiple locations on the epicardial tissue.

Figure 11A:
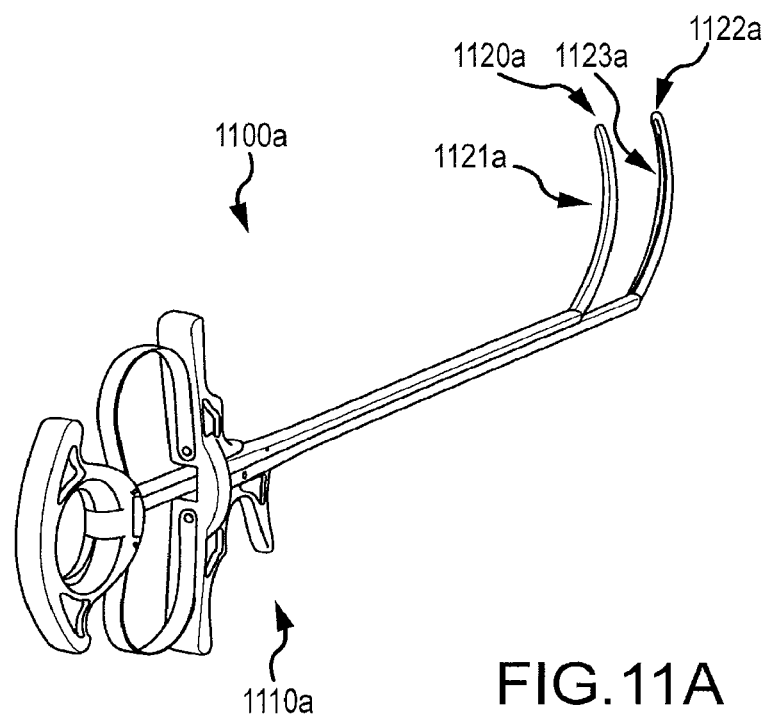
FIG. 11A depicts a tissue treatment system according to embodiments of the present invention.
Figure 11B:
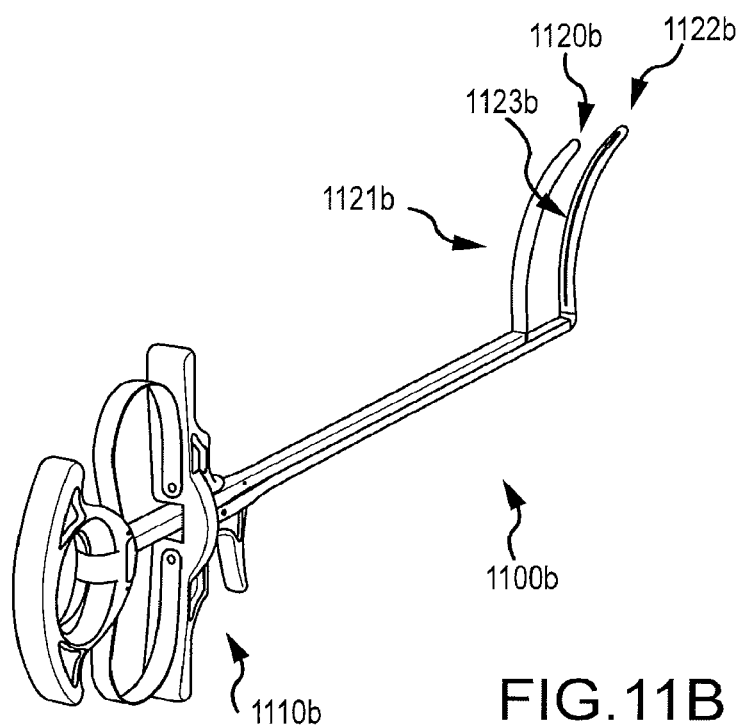
FIG. 11B depicts a tissue treatment system according to embodiments of the present invention.

FIGS. 11A and 11B show exemplary ablation devices or tissue treatment systems according to embodiments of the present invention. As shown in FIG. 11A, ablation device 1100a includes a handle 1110a disposed toward a proximal end of the device, and two bipolar ablation clamps 1120a, 1122a disposed toward a distal end of the device. The ablation clamps are curved, so that for each clamp 1120a, 1122a, a concave portion of arc 1121a, 1123a, faces toward handle. Each clamp can be coupled with or configured to at least partially receive one or more stimulation electrodes, one or more coagulation electrodes, or both. As depicted here, the convex side of arc 1121a, and the concave side of arc 1123a can each be in connectivity with a respective ablation and monitoring assembly. FIG. 11B illustrates an ablation device 1100b having a handle 1100b disposed toward a proximal end of the device, and two bipolar ablation clamps 1120b, 1122b disposed toward a distal end of the device. The ablation clamps are curved, so that for each clamp 1120b, 1122b, a convex portion of arc 1121b, 1123b, faces toward handle. Each clamp can be coupled with or configured to at least partially receive one or more stimulation electrodes, one or more coagulation electrodes, or both. As depicted here, the concave side of arc 1121b, and the convex side of arc 1123b can each be in connectivity with a respective ablation and monitoring assembly. During use, the tissue treatment system can be used to contact the cardiac tissue, similar to the approach depicted in FIG. 10. The curved or contoured shape of the clamps allow the treatment system to be placed on the heart without impinging upon the pulmonary veins. Hence, there is an increased likelihood of ablating tissue of the atrium, as opposed to ablating tissue of the pulmonary veins themselves. Treatment systems 1100a, 1100b are well suited for use in surgical methods where access ports are not employed. For example, the treatment systems can be inserted into a patient via a 3-4 inch thoracotomy. In use, the clamps are placed at or near the ostia, and actuated until the opposing clamp members are approximately 2-5 millimeters apart. This action serves to collapse the atrium near the pulmonary veins. An ablation is performed, and the clamping pressure is released thus allowing the atrium to return to the uncompressed state. The tissue treatment systems can have a spring loaded mechanism that allows an indirect connection between the handle and the clamp members or jaws. Hence, during the initial stage of the clamping process, there is a 1:1 ratio between movement of the handle and movement of the clamp members or jaws. However, during the later stage of the clamping process when the clamp members or jaws are sufficiently close to one another, optionally applying sufficient pressure on the atrium, there is not a 1:1 ration between movement of the handle and movement of the clamp members or jaws. Rather, a handle movement results in a smaller corresponding movement of the clamp members and jaws. The ablation and monitoring assemblies can be configured as inserts that are removable with respect to the clamp members or jaws. According to some embodiments, the ablation and monitoring assemblies may be disposable, replaceable, or both, and the clamp or support member can be sterilizable, reusable, or both.

In some embodiments, a tissue treatment system can include an ablation and monitoring assembly having energy transmission and stimulation elements. Optionally, an ablation and monitoring assembly can include one or more tissue stimulation electrodes or elements. In some cases, stimulation electrodes or elements can be or include tip electrodes that are about 1 mm to 2 mm in length, and about 2 mm to 4 mm in diameter. In some cases, a stimulation electrodes can be about 1 mm to 3 mm from a coagulation electrodes. A stimulation electrode may, optionally, be a ring electrode. For example, a stimulation electrode can be a relatively small ring electrodes (e.g. too small to form transmural myocardial lesions) that is about 0.5 mm to 2 mm in length and about 1.5 mm to 3 mm in diameter. According to some embodiments, a stimulation and a coagulation are disposed on a common support structure.

A tissue treatment system may be used to test the quality of lesions formed during a lesion formation procedure in a variety of ways. For example, in the context of the treatment of atrial fibrillation, a tissue treatment system may be used to form lesions around one or more pulmonary veins to isolated the left atria from arrhythmias that originate in the pulmonary veins. In one exemplary procedure, a clamp may be positioned around a pair of pulmonary veins and one or more coagulation electrodes can form a lesion around the pair. One or more stimulation electrodes may be used to supply a bipolar pacing pulse (e.g. about 20 mA) on the side of the lesion opposite the left atrium. An operator or physician can determine whether or not a therapeutic lesion (e.g. "complete block") has been formed by observing the left atrium. If the pacing pulse is able to cross the lesion, the heart will beat faster (e.g. 120 beats/minute). This may be determined by observation or by use of an ECG machine that is monitoring the heart. In some cases, additional coagulation will be required or desired to complete or further develop the lesion. The failure to stimulate the heart from the side of the lesion opposite the left atrium can be, on the other hand, indicative of the formation of a therapeutic lesion. Nevertheless, because muscle bundles are not always connected near the pulmonary veins, it may be preferable that the stimulation energy be applied to a number of tissue areas on the side of the lesion opposite the left atrium to reduce the possibility of false negatives.

In some cases, stimulation electrodes or elements may then be used to monitor tissue within the region that was intended to be isolated. In the context of pulmonary vein isolation, for example, stimulation electrodes may be placed in contact with viable tissue on the pulmonary vein side of the lesion. Local activation within the isolated region from the heart's natural stimulation is generally indicative of a gap in the lesion. Embodiments of the present invention encompass autodetection techniques that can be implemented when pulmonary veins are isolated with a clamp.

Stimulation electrodes may also be used in a unipolar operation similar to a bipolar operation. In some cases, electrodes can be placed on opposite sides of a continuous linear or curvilinear lesion. For example, one electrode may be placed within the left atrium and another electrode may be placed on the pulmonary vein side of a pulmonary vein ostium. A pulse of stimulation energy (e.g. about 10 mA) may be applied to viable tissue on one side of the lesion by one electrode and the viable tissue on the other side of the lesion may be monitored with the other electrode to detect whether or not there is local excitation from the pulse of stimulation energy. A tissue treatment system can be used to determine whether or not or to what extent a lesion is transmural. In some cases a first electrode and a second electrode may be placed on opposite surfaces of the lesion (e.g. the epicardial and endocardial surfaces, or two epicardial surfaces).

According to some embodiments, one or more stimulation electrodes may be used to test a lesion formed with one or more coagulation electrodes, without moving a clamp. For example, after a lesion is formed, a pulse of stimulation energy (e.g. about 10 mA) may be applied to viable tissue on one side of the lesion by one or more stimulation electrodes, while viable tissue on the other side of the lesion may be monitored with one or more stimulation electrodes to detect local excitation from the pulse of stimulation energy. The tissue treatment system can measure the conduction delay between the delivery of the pulse to the tissue on one side of the lesion and the detection of the local activation on the other side of the lesion. The conduction delay generally is indicative of the quality of the lesion.

An exemplary tissue treatment system can include an ESU that supplies and controls power to an electrophysiology clamp apparatus or other ablation and monitoring assembly. In some cases, an electrophysiology clamp apparatus includes clamp and a tissue coagulation assembly that may be secured to the clamp. According to some embodiments, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. In some cases the clamp members and handles are not mounted on the opposite ends of the same arm, but instead the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

A tissue treatment system can include a clamp having a pair of rigid arms that are pivotably connected to one another by a pin. The proximal ends of the arms can be respectively connected to a pair handle members, while the distal ends can be respectively connected to a pair of clamp members. The clamp members may be rigid or malleable and, if rigid, may be linear or have a pre-shaped curvature. A locking device can lock the clamp in a closed orientation, and prevent or inhibit relative movement of the clamp members, thereby defining a predetermined (or preset) spacing between the clamp members. Often, a clamp is configured so that clamp members, or optionally ablation or monitoring elements coupled thereto, are in parallel alignment. A clamp can be configured for use with a pair of soft, deformable inserts that may be removably carried by the clamp members and allow the clamp to firmly grip a bodily structure without damaging the structure. To that end, the clamp members can each include a slot that is provided with a sloped inlet area and the inserts include mating structures that are removably friction fit within the slots. An ablation and monitoring assembly, or components thereof, can be mounted on the clamp members, optionally in place of the inserts. In some cases a first ablation member can be coupled with a first clamp member, and a second ablation member can be coupled with a second clamp member.

Coagulation electrodes can be provided in the form of wound, spiral closed coils. The coils can be made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Exemplary coil electrodes are disclosed in U.S. Pat. Nos. 5,797,905, and 6,245,068, the content of each of which is incorporated herein by reference. In some cases, electrodes may be in the form of solid rings of conductive material, like platinum, or can include a conductive material, like platinum-iridium or gold, coated upon the device using conventional coating techniques or an ion beam assisted deposition (IBAD) process. In some cases, an undercoating of nickel, silver or titanium can be applied. The electrodes can also be in the form of helical ribbons. The electrodes can also be formed with a conductive ink compound that is pad printed onto a non-conductive tubular body. An exemplary conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Still other types of electrodes are formed from electroless plated copper on a polyimide film or tubular substrate. Gold, nickel or silver can be plated over the copper for electrochemical stability and improved biocompatibility. The plating can be applied in continuous form (e.g. up to about 1-2 cm in length) or can be applied in a pattern that is designed to improve current density distributions and/or electrode flexing characteristics. Temperature sensors (e.g. thermocouples) may be incorporated into the electrode structure by placing the temperature sensors in a channel in the polyimide film or tubular substrate and then plating over them.

In some cases, electrodes are about 1.5 cm to 4 cm in length with about 1 mm to 3 mm spacing, which can result in the creation of continuous lesion patterns in tissue when coagulation energy is applied simultaneously to adjacent electrodes. The length of an electrode on one energy transmission device on a first clamp member can be the combined length of multiple electrodes, including the spacing therebetween, on another energy transmission device on a second clamp member. Relatedly, the overall electrode length on the first and second energy transmission devices can be the same. In some embodiments, first and second energy transmission devices can be provided with respective mounting devices that may be used to mount a tissue coagulation assembly in general, and an energy transmission devices in particular, on the clamp. Additionally, although the configuration of a tissue coagulation assembly may vary from application to application to suit particular situations, an exemplary tissue coagulation assembly is configured such that an electrode on one clamp member will be parallel to an electrode on an opposing clamp member when the clamp is in the closed orientation. In some cases, one or more temperature sensors, such as thermocouples or thermistors, may be located on, under, abutting the longitudinal end edges of, or in between, the electrodes. A reference thermocouple may also be provided. Tissue treatment system can also include elements or features described in U.S. patent application Ser. Nos. 10/727,143 and 10/727,144 filed Dec. 2, 2003; 11/031,629 filed Jan. 8, 2005; and 11/186,149 filed Jul. 20, 2005. The content of each of these applications is incorporated herein by reference.

Figure 12:
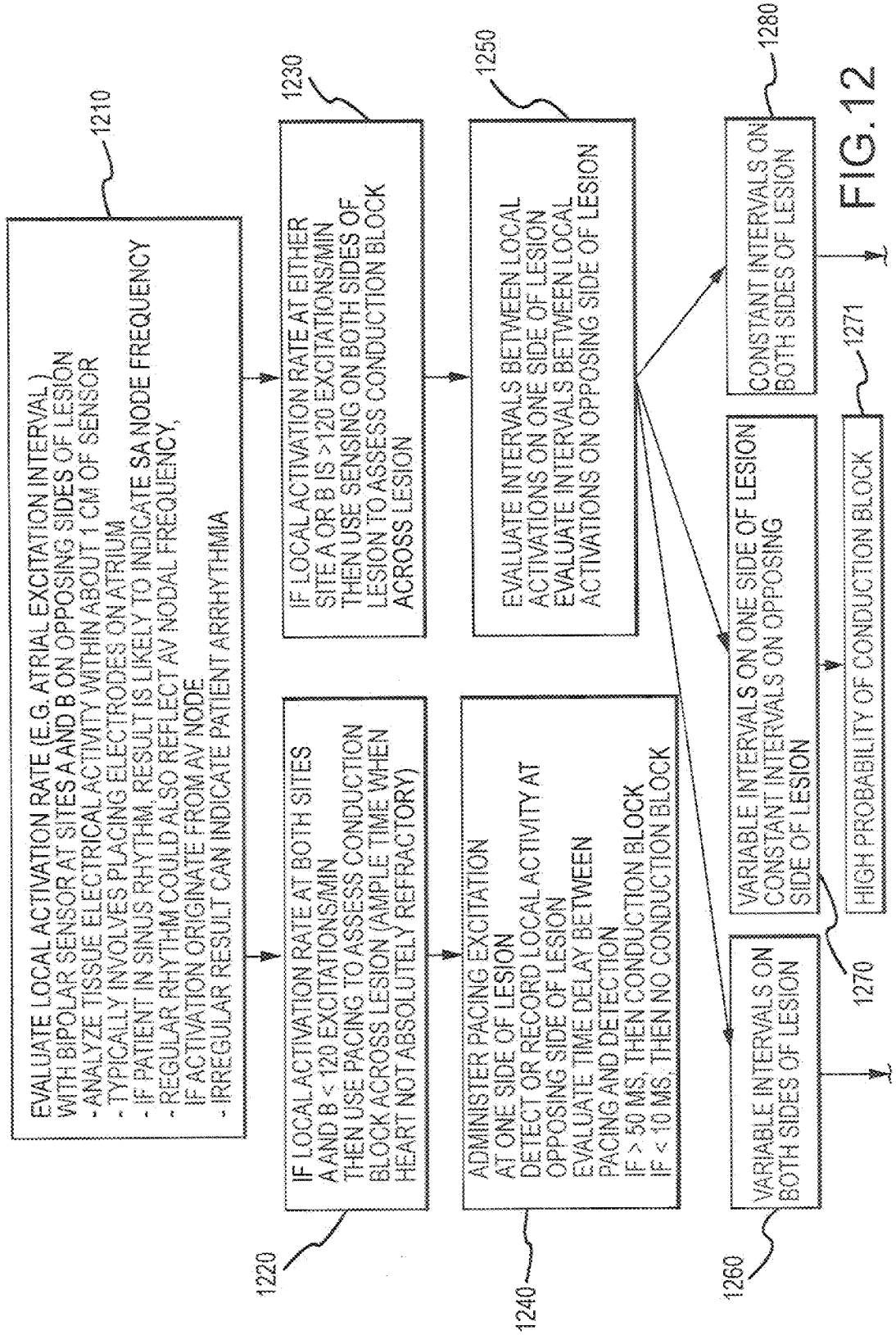
FIGS. 12 and 12A illustrate an automated conduction delay process according to embodiments of the present invention.
Figure 12A:
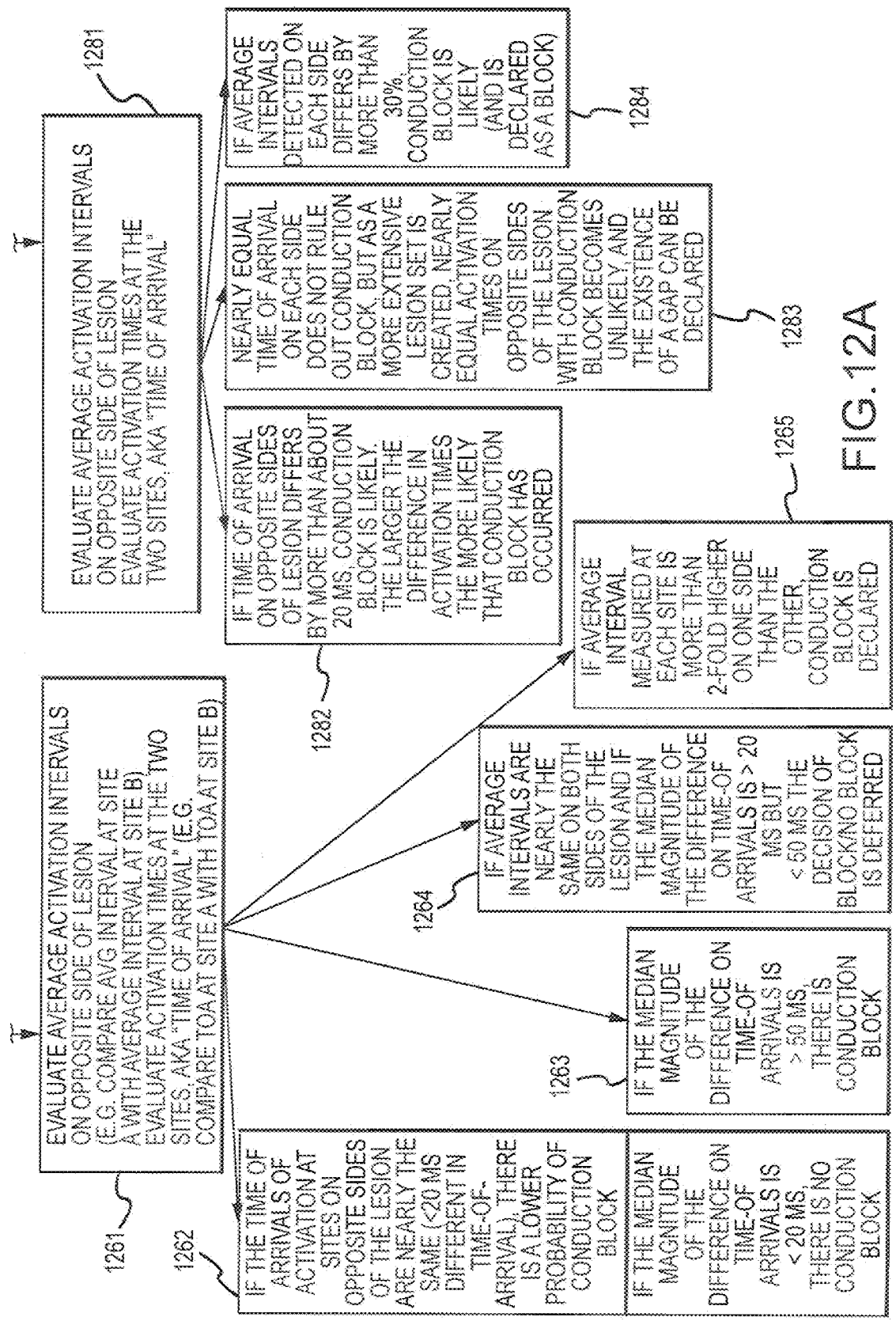

Embodiments of the present invention also encompass systems and methods for performing a conduction block procedure independent of patient rhythm. FIGS. 12 and 12A depicts an exemplary automated conduction delay process 1200. As shown here, process 1200 include determining whether pacing or sensing should be used to assess conduction delay from one side of a lesion to the other. The determination can be based on various factors. For example, the determination can be based on features of a heart rate of the individual, features of beat-to-beat intervals of the individual, or both. As indicated in step 1210, the process can include evaluating a local activation rate, for example an atrial excitation interval, with bipolar sensor at sites A and B on opposing sides of a lesion. Where the process involves evaluation of atrial electrical activity, the method may include placing one or more sensors or electrodes on the atrium of the patient. Such evaluation techniques may involve analyzing tissue electrical activity at or near a sensor, or within a certain distance from the sensor. In some cases, tissue electrical activity within about 1 cm of a sensor is analyzed. When evaluating atrial activity, the results of the evaluation are likely to indicate or reflect an SA node frequency if the patient is in sinus rhythm. In some cases, a regular rhythm may also reflect AV nodal frequency, if the activation originates from the AV node. Irregular electrical activity in the atrium may indicate that the patient is in arrhythmia.

If the local activation rate at site A and the local activation rate at site B are both less than a certain excitation rate, then pacing can be used to assess any conduction block across the lesion, as indicated by step 1220. For example, if the local activation rate at both sites A and B is less than 120 excitations per minute, then the method may include performing a pacing procedure on the patient and analyzing the status of a conduction block based on an evaluation of cardiac activity in response to the pacing. When the local activation rate at site A and the local activation rate at site B are both sufficiently infrequent, pacing can be used as there is ample time when the heart is not in an absolutely refractory state or interval. A local activation rate of less than 120 excitations per minute can correspond to a time between excitations of greater than 500 milliseconds.

In some cases, there may be atrial fibrillation both on the inside and the outside of a box lesion, particularly when the patient heart size is relatively large. In some cases, there may be a tachycardia on either side of the lesion. Optionally, the tachycardia may originate from a pulmonary vein. In a diseased heart, it is often the case that a PV can pace itself, or is self pace-making, and that the PV can pace at a fast rate. In some cases, a PV can continuously pace at a high rate. It may be possible to determine whether there is a regular rhythm by disconnecting or isolating a small region around or near a PV, separate from the rest of the heart. The patient may have on one side of the lesion (e.g. PV side) a very fast regular rate that is difficult or impossible to pace over, and on the other side of the lesion an atrial fibrillation. According to some embodiments of the present invention, the presence or detection of a rapid rate on both sides may not provide conclusive evidence that a conduction block has been formed or otherwise exists.

As depicted by step 1240, a pacing protocol may include administering a pacing excitation at one side of a lesion, and detecting or recording local activity at an opposing side of the lesion. The protocol also includes evaluating a time delay between administration of the pacing excitation on one side and detection of local activity on the other side. If a delay between the administered excitation at site A and the detected activity at site B, for example, is sufficiently great, then it may be determined that a conduction block exists. For example, if the delay is greater than about 50 milliseconds, then a determination may be made that there is a conduction block between site A and site B. If, on the other hand, a delay between the administered excitation at site A and the detected activity at site B, for example, is not sufficiently great, then it may be determined that a conduction block does not exist. For example, if the delay is less than about 10 milliseconds, then a determination may be made that there is no conduction block between site A and site B. In some cases, the rate of excitation spread is about 1 meter per second. Hence, if the expected distance of travel for the excitation is about 1 centimeter, then the travel time is about 10 milliseconds, where there is no block. If there is a block, the excitation is typically forced to travel around the block, and hence the travel time is greater. For example, the travel time may be 50 milliseconds or more.

If either the local activation rate at site A or the local activation rate at site B is greater than a certain excitation rate, then a sensing protocol can be used to assess any conduction block across the lesion, as indicated by step 1230. A sensing protocol typically involves sensing electrical activity on both sides of a lesion. According to some embodiments, variable intervals between local activations on either side of a lesion suggests indicates atrial fibrillation on that side (or sides). Atrial fibrillation can be characterized by highly variable intervals, and average short times between successive activations (e.g. high activation frequency). As illustrated by step 1250, a sensing protocol can include evaluating intervals between local activations on one side of lesion, evaluating intervals between local activations on an opposing side of lesion, or both. For example, the intervals between local activations on one side of a lesion may be variable, and the intervals between local activations on an opposing side of the lesion may be variable, as indicated by step 1260. In such instances, as illustrated in step 1261, a sensing protocol may include evaluating average activation intervals on opposite sides of a lesion. For example, the method may include comparing an average activation interval at site A on one side of a lesion with an average activation interval at site B on an opposing side of the lesion. The sensing protocol may also include evaluating activation times, or time of arrival (TOA) at sites A and B, as further illustrated in step 1261. For example, the method may include comparing the time of arrival of an activation at site A with a time of arrival of an activation at site B. TOA can be a useful parameter to evaluate when assessing conduction delay, as it may be desirable to ascertain activation time, in relative sense, from one side to another, separate from knowing average of activations at both sides.

In some cases, a good conduction block may exist and the average activation time on both sides may be similar, yet both sides are being stimulated independently. In pacing, the activation direction may be known. However with sensing techniques, the activation direction may not be known. Hence, it may be desirable or helpful to be able to make inferences as to where an activation is originating from, or as to the spatial relationships between sites A and B or the expected travel time between A and B.

As indicated in step 1262 of the process, if the time of arrival of activation at site A on one side of the lesion and the time of arrival of activation at site B on an opposite side of the lesion are sufficiently similar, then it may be determined that there is no conduction block, or that there is a lower probability of a conduction block. For example, if the TOA at sites on opposite sides of the lesion are nearly the same, or there is a difference between the TOA's of less than about 20 milliseconds, then it may be concluded that there is no conduction block, or that there is a lower probability of a conduction block. In some embodiments, the determined probability of the existence of a conduction block decreases as the difference in the time of arrivals decreases. In some embodiments, if the median magnitude of the difference on time-of arrivals is less than about 20 milliseconds, then it may be determined that there is no conduction block.

As indicated in step 1263, if the median magnitude of the difference between the TOAs is sufficiently large, then it may be possible to determine that there is a conduction block between the sites. For example, in some embodiments if the median magnitude of the difference on time-of arrivals is greater than about 50 milliseconds, then the method may include a determination that a conduction block exists. In some embodiments, the determined probability of the existence of a conduction block increases as the difference in the time of arrivals increases. Options 1262 and 1263 may assume, for example, that the average interval is substantially the same. Relatedly, a sufficiently large difference in the average intervals may indicate a disconnection.

According to step 1264, the decision or determination as to whether a block exists may be deferred. For example, if the average intervals are sufficiently similar or nearly the same on both sides of the lesion and if the median magnitude of the difference on time-of arrivals is greater than about 20 milliseconds and less than about 50 milliseconds, then the method may include deferring any decision regarding the existence of a conduction block.

Step 1265 indicates that if the average interval measured at each site is more than twofold higher on one side than the other, then it is possible to determine that a conduction block exists.

As noted above, a sensing protocol can include evaluating intervals between local activations on one side of lesion, evaluating intervals between local activations on an opposing side of lesion, or both. For example, the intervals between local activations on one side of a lesion may be variable, and the intervals between local activations on an opposing side of the lesion may be constant, as indicated by step 1270. In such circumstances, the method may include making a determination that a conduction block exists or that there is a high probability of a conduction block, as indicated by step 1271.

Step 1280 of the method reflects a situation where the intervals between local activations on one side of the lesion are constant and intervals between local activations on an opposing side of the lesion are constant. In such instances, as illustrated in step 1281, a sensing protocol may include evaluating average activation intervals on opposite sides of a lesion. For example, the method may include comparing an average activation interval at site A on one side of a lesion with an average activation interval at site B on an opposing side of the lesion. The sensing protocol may also include evaluating activation times, or time of arrival (TOA) at sites A and B. For example, the method may include comparing the time of arrival of an activation at site A with a time of arrival of an activation at site B.

As indicated in step 1282 of the process, if the time of arrival of activation at site A on one side of the lesion and the time of arrival of activation at site B on an opposing side of the lesion are sufficiently distinct, then it may be determined that there is a conduction block, or that there is a higher probability of a conduction block. For example, if the TOA at sites on opposite sides of the lesion are largely dissimilar, or there is a difference between the TOA's of more than about 20 milliseconds, then it may be concluded that there is a conduction block, or that there is a higher probability of a conduction block. In some embodiments, the determined probability of the existence of a conduction block decreases as the difference in the time of arrivals decreases. In some embodiments, if the median magnitude of the difference on time-of arrivals is less than about 20 milliseconds, then it may be determined that there is no conduction block.

According to step 1283 of the method, nearly equal time of arrivals on each side of a lesion does not rule out the existence of a conduction block at the lesion. However, as a more extensive lesion set is created, nearly equal activation times on opposite sides of the lesion with conduction block becomes more unlikely and the existence of a gap can be declared. As a lengthier or more extensive lesion or lesion set is created, the probability of a conduction block forming increases. Thus, in some cases, as more lesions are formed, it is unlikely to have small differences in time of arrival and not have a conduction block.

If the average intervals are substantially different, then the median magnitude of difference may be unlikely to be small. If the heart rate differs sufficiently, for example by 60%, then it may be more unlikely to have a small median magnitude of difference.

Step 1284 of the method reflects a circumstance where if the average intervals detected on each side of a lesion differ by more than 30%, then it is possible to determine that a conduction block is likely. This can be true regardless of the median magnitude of difference of time of arrivals.

According to some embodiments, if the heart rate is less than about 120 beats per minute, the beat-to-beat interval is less than about 500 milliseconds, and the beat-to-beat interval between detected local activations is relatively constant (e.g. less than 15% variation of measured intervals about the mean), then pacing can be used to assess conduction delay. If those conditions are not met, then conduction block across the lesion can be assessed by sensing on both sides of the lesions. For example, if the local heart rate is even, but fast (excitation interval<500 ms), if time of arrival on opposite sides of a lesion differs by more than about 20 ms, conduction block is likely. A larger difference in activation times corresponds to a higher likelihood that conduction block has occurred. Nearly equal times of arrival on each side does not rule out a conduction block, but as a more extensive lesion set is created, nearly equal activation times on opposite sides of the lesion with conduction block becomes unlikely, and a determination can be made that a gap exists. If average intervals detected on each side differs by more than 30%, the it is possible to determine that conduction block is likely and to declare the existence of a block. If the detected intervals are variable at a local site then average activation intervals can be determined on each side, and differences in activation times at the two sites can be determined. Typical activation intervals are 100-250 ms during atrial fibrillation. With no conduction block, the time of arrivals of activation at sites on opposite sides of the lesion (e.g. about 1 cm apart) are usually nearly the same (e.g. <20 ms different in time-of-arrival). If the median magnitude of the difference on time-of arrivals is <20 ms, then it is possible to determine that there is no conduction block. If the average interval measured at each site is more than 2-fold higher on one side than the other, it is possible to determine that there is a conduction block. If the median magnitude of the difference on time-of arrivals is >50 ms, then it is possible to determine that there is a conduction block. In cases where the average intervals are nearly the same on both sides of the lesion and if the median magnitude of the difference on time-of arrivals is >20 ms but <50 ms, then a method may involve deferring a determination as to whether or not a conduction block exists.

In some embodiments, a heart rate of 72 beats per minute correlates with an 800 millisecond interval between excitations. If it is not possible to defibrillate a patient to a normal or good rhythm, then it may be desirable to use sensing to assess conduction delay across a lesion to evaluate conduction block. In normal sinus rhythm, the ratio of atrial excitation to ventricular excitation is 1:1. In atrial fibrillation, there may be multiple atrial excitations corresponding to only one ventricular excitation. Pacing typically involves excitation at a rate 10% faster than atrial excitation. However, it may be undesirable to pace where the atrial excitation rate is 130 excitations per minute, due to safety reasons.

According to some embodiments, conduction block assessment techniques involve evaluating activations that occur prior to or subsequent to a particular activation. For example, a method may involve considering an activation on one side of a lesion, and also considering one or more activations occurring prior to the activation, subsequent to the activation, or both. This approach can be useful in evaluating local activation direction, which may be highly variable between successive activations. Data regarding the activations can be maintained in a circuit buffer.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of operating a tissue treatment system during a cardiac surgical procedure, comprising:
    placing an ablation and monitoring assembly of the tissue treatment system at a patient tissue treatment site, the ablation and monitoring assembly comprising a first ablation element, a second ablation element, a stimulation electrode and a sensing electrode;
    applying a first ablative energy to a first tissue location via the first ablation element and simultaneously applying a second ablative energy to a second tissue location via the second ablation element;
    monitoring a condition of the first tissue location by delivering a stimulation energy to the first tissue location with the stimulation electrode, sensing a tissue near the first tissue location with the sensing electrode to detect whether the tissue near the first tissue location is sufficiently stimulated in response to the stimulation energy where monitoring the condition occurs while applying the first ablative energy and the second ablative energy, wherein the sensing electrode detects a stimulation response during delivery of one or more of the first ablative energy and the second ablative energy;
    modulating application of the first ablative energy to the first tissue location while monitoring the condition of the first tissue location and while maintaining application of the second ablative energy to the second tissue location via the second ablation element, wherein the second ablation element maintains the second ablative energy;
    sensing a tissue near the second tissue location to determine a conduction block status of the second tissue location;
    evaluating a first local activation rate at a first site on a first side of a conduction block;
    evaluating a second local activation rate at a second site on a second side of the conduction block;
    performing a pacing procedure to assess a conduction delay if both the first local activation rate and the second local activation rate are less than a predetermined excitation rate; and
    performing a sensing procedure to assess the conduction delay if either of the first local activation rate or the second local activation rate exceed the predetermined excitation rate.

2. The method of claim 1, further comprising evaluating an electrocardiogram of the tissue near the first tissue location.

3. The method of claim 1, wherein the monitoring step comprises visually inspecting the tissue near the first tissue location.

4. The method of claim 1, wherein the ablation and monitoring assembly comprises a plurality of stimulation electrodes.

5. The method of claim 1, wherein the patient tissue treatment site comprises epicardial tissue at or near one or more pulmonary veins of the patient.

6. The method of claim 1, comprising placing the ablation and monitoring assembly at the patient tissue treatment site with an obturator and introducer assembly.

7. The method of claim 1, wherein the tissue treatment system comprises a tissue contacting assembly, and the ablation and monitoring assembly is at least partially disposed within the tissue contacting assembly.

8. The method of claim 1, further comprising determining whether the ablation and monitoring assembly is in sufficient contact with the patient tissue treatment site.

9. The method of claim 1, wherein the monitoring step comprises detecting a conduction block at the first tissue location.

10. The method of claim 1, comprising contacting the patient tissue treatment site with a suction mechanism of the tissue treatment system.

11. The method of claim 1, wherein the first ablation element comprises a monopolar electrode.

12. The method of claim 1, wherein the first ablation element comprises a bipolar electrode.

13. The method of claim 1, further comprising continuing application of the first ablative energy to the first tissue location after the tissue near the first tissue location ceases to be stimulated in response to the stimulation energy.

14. A method of operating a tissue treatment system during a cardiac surgical procedure, comprising:
    placing an ablation and monitoring assembly of the tissue treatment system at a patient tissue treatment site, the ablation and monitoring assembly comprising an ablation element a stimulation electrode and a sensing electrode;

applying a first ablative energy to a first tissue location via a first portion of the ablation element and simultaneously applying a second ablative energy to a second tissue location via a second portion of the ablation element;

monitoring a condition of the first tissue location by delivering a stimulation energy to the first tissue location with the stimulation electrode, sensing a tissue near the first tissue location with the sensing electrode to detect whether the tissue near the first tissue location is sufficiently stimulated in response to the stimulation energy, where monitoring the condition occurs while applying first ablative energy and the second ablative energy, wherein the sensing electrode detects a stimulation response during delivery of one or more of the first ablative energy and the second ablative energy;

modulating application of the first ablative energy to the first tissue location while monitoring the condition of the first tissue location and while maintaining application of the second ablative energy to the second tissue location via the second ablation element, wherein the second ablation element maintains the second ablative energy;

sensing a tissue near the second tissue location to determine a conduction block status of the second tissue location;

evaluating a first local activation rate at a first site on a first side of a conduction block;

evaluating a second local activation rate at a second site on a second side of the conduction block;

performing a pacing procedure to assess a conduction delay if both the first local activation rate and the second local activation rate are less than a predetermined excitation rate; and performing a sensing procedure to assess the conduction delay if either of the first local activation rate or the second local activation rate exceed the predetermined excitation rate.

15. The method of claim 14, further comprising continuing application of the first ablative energy to the first tissue location after the tissue near the first tissue location ceases to be stimulated in response to the stimulation energy.

* * * * *